(12) United States Patent
Evdokimov et al.

(10) Patent No.: US 6,246,470 B1
(45) Date of Patent: Jun. 12, 2001

(54) METHOD FOR DETERMINATION OF A BIOLOGICALLY ACTIVE SUBSTANCE IN AN ANALYZED LIQUID AND DEVICE FOR ITS REALIZATION

(75) Inventors: Jury Mikhailovich Evdokimov; Sergei Gennadievich Skuridin; Boris Alexandrovich Chernukha, all of Moscow; Evgeny Leonidovich Mikhailov; Oleg Nikolaevich Kompanets, both of Moskovskaya oblast; Sergei Nikolaevich Romanov, Moscow; Vladimir Vasilievich Kolosov, Moskovskaya oblast, all of (RU)

(73) Assignee: Institut Molekulyarnoi Biologi Imeni V.A. Engelgardita Rossiiskoi Akademii Nauk (RU)

( * ) Notice: Subject to any disclaimer, the term of this patent is extended or adjusted under 35 U.S.C. 154(b) by 0 days.

(21) Appl. No.: 09/101,701
(22) PCT Filed: Nov. 14, 1997
(86) PCT No.: PCT/RU97/00358
  § 371 Date: Jul. 15, 1998
  § 102(e) Date: Jul. 15, 1998
(87) PCT Pub. No.: WO98/22804
  PCT Pub. Date: May 28, 1998

(30) Foreign Application Priority Data
Nov. 15, 1996 (RU) ................................................ 96122087

(51) Int. Cl.$^7$ .................................................... G01N 21/00
(52) U.S. Cl. .......................... 356/73; 356/364; 356/367
(58) Field of Search ............................ 356/73, 364, 367, 356/368

(56) References Cited

U.S. PATENT DOCUMENTS 4,467,204  8/1984  Kysilka et al. .

(List continued on next page.)

FOREIGN PATENT DOCUMENTS 2529338  6/1983  (FR) .
2016888  7/1994  (RU) .
2032895  4/1995  (RU) .

OTHER PUBLICATIONS

Modern Methods of Biochemistry, Ed. by V. N. Orekhovich; M: Medicine. 1968, p. 372.

(List continued on next page.)

Primary Examiner—Frank G. Font
Assistant Examiner—Roy M. Punnoose
(74) Attorney, Agent, or Firm—Ostrolenk, Faber, Gerb & Soffen, LLP

(57) ABSTRACT

The present invention allows quickly, simply, precisely and with high sensitivity to determine the presence and concentration of any biologically active substances capable to interact with linear double-stranded DNA molecules in any liquids including biological liquids. The essence of the offered method consists that the lyotropic liquid-crystalline cholesteric DNA dispersion is formed in an aqueous-salted solution of a polymer, neutral in respect to DNA, of the linear double-stranded DNA molecules of a low molecular mass immediately before mixing with an analyzed liquid containing the determined substance, thereat the liquid for the analysis is prepared by mixing with the specified polymer under conditions, when the optical properties of the lyotropic liquid-crystalline DNA dispersion are not broken, then through the sample obtained as a result of mixing of the prepared analyzed liquid with the liquid-crystalline DNA dispersion the circular-polarized light is passed, and the optical signal is registered at two wavelengths, one of them is in the region of the DNA absorption, and another one is in the region of absorption of the biologically active substance, then the ratio between these two signals is calculated, and concentration of the biologically active substance is determined on this ratio using the calibration curve. The offered device contains a wavelength selector (2) having an electrodynamic driver (22) of a positional type and at least one optical element (26, 27, 28) fixed on a motor (33) shaft (35) of the specified driver (22).

15 Claims, 10 Drawing Sheets

U.S. PATENT DOCUMENTS

| | | |
|---|---|---|
| 4,796,995 | 1/1989 | Salzman et al. . |
| 4,988,199 | 1/1991 | Paul . |
| 5,209,231 * | 5/1993 | Cote et al. .......................... 356/367 |

OTHER PUBLICATIONS

Methods of Practical Biochemistry, Ed. by B. Williams, K. Wilson. *M.: World*, 1978, p. 256.

Vysokomolekuyyarnye soedineniya, pp. 2403–2410;.

High–Performance Liquid Chromatographic Determination fo Mitoxantrone in Plasma Utilizing Non–Bonded Silica Gel for Solid–Phase Isolation to Reduce Adsorptive Losses on Glass During Sample Preparation; *Journal of Chromatography*, 465 (1989) 75–86.

Phase I–II Intraperitoneal Mitoxantrone; Maria O. Nicoletto et al; *Eur J Cancer*, Vo. 29A, No. 9, pp. 1242–1248 (1993).

Identification of Human Urinary Mitoxantrone Metabolites, F.S. Chiccarelli, et al. *Cancer Research* 46, 4858–4861, (1986).

The liquid–crystalline phases of double–stranded nucleic acids; Yu.M. Yeddokimov et al; *Liquid Crystals*: vol. 3, No. 11, 1443–1459 (1988).

Spectropolarimeter; *Jasco Corporation*, Jun. 1990.

Dichrograph R.J. Mark III.

* cited by examiner

METHOD FOR DETERMINATION OF A BIOLOGICALLY ACTIVE SUBSTANCE IN AN ANALYZED LIQUID AND DEVICE FOR ITS REALIZATION

FIELD OF THE INVENTION

The present invention concerns to the medical engineering and the pharmaceutical industry, and more particularly—to the way of determination in an analyzed liquid of a biologically active substance and the device for its realization.

The offered invention can be used in medical and clinical biochemistry and also in the molecular pharmacology at research of pharmaco-kinetics of biologically active substances, in pharmaceutical industry and in ecology. The most effective use of the present invention is in clinical biochemistry.

DESCRIPTION OF THE RELATED ART

The basic problem at rational pharmaco-kinetics of biologically active substances (BAS), in particular, synthetic and half-synthetic antitumor substances, influencing a possibilities of effective therapy, is reduced to speed and accuracy of determination of concentration of these substances in biological liquids (blood, plasma of blood, urea, etc.) after treatment of patients with certain amount of an antitumor substance.

Two basic groups of methods are known for determination of the presence and the efficiency of "action" of BAS, basic "target" of which are molecules of double-stranded nucleic acids.

The first group is formed by the biological methods [Modern methods in biochemistry. Ed. by V. N. Orekhovich. M.: Medicine. 1968, p.372; Methods of practical biochemistry. Ed. by B. Williams, K. Wilson. M.: World, 1978, p. 256]. They are based on the investigation of well-registered changes in well-described genetic systems (bacteria, bacteriophages, cultures of cells) after their treatment with BAS. These methods are realized by means of the standard microscopes. However, on a way of BAS penetration, the modification of their structures can However, on a way of BAS penetration, the modification of their structures can take place influencing the accuracy of the establishment of correlation between the structure of BAS, its concentration and the biological activity. In addition, the specified methods differ by duration of realization of the experiment (from days till weeks).

The second group includes the physico-chemicalical methods or their different combinations. Since 1980, a few methods of determination of BAS, in particular, derivatives of the anthraquinone group have been offered. Among them there are various versions of the radioimmune analysis [Nicolau G., Szucs-Myers V., McWilliams W., Morrison J., Lanzilotti A. (1985). Investigational New Drugs, 3: pp.51–56 ], the high-pressure thin-layer chromatography [Avramis V. (1982), Abstract. Pharmacologist, 24, p.241; Ehninger G., Proksch B., Hartmann F., Gartner H. V., Wilms K. (1984). Cancer Chemotherapy and Pharmacology, 12, pp.50–52 ], the method of replacement of DNA bound ethydiumbromide [Horvath J. J., Gueguetchkeri M., Gupta A., Penumatchu D., Weetall H. H., (1995), Biosensor and Chemical Sensor Technology. Ed. by Rogers K. R. et al., Washington, ASC Symp.Ser. 613, pp. 45–60]. The greatest application has been gained by the columnar high-pressure-liquid-chromatography (HPLC) [Chiccarelli F. S., Morrison J. A., Cosulich D. B., Perkinson N. A., Ridge D. N. (1986), Cancer Research, 46, pp. 4858–4861; Lin K. T., Rivard G. E., Leclerc J. M. (1989). J. Chromatography, 465, pp.75–86], carried out by the standard chromatographic devices.

The application of the HPLC method for determination of one of important anthraquinone—mithoxantrone (MX) has been described rather recently [Nicoletto M. O., Padrini R., Ferrazi E., Nascimben O., Visona E., Tumolo S., Palumbo M., Cossta L., Vinante O., Monfardini S., Fiorentino M. V. (1993). Eur. J. Cancer. 29A, pp.1242–1248]. According to this method, MX and products of its methabolism are extracted from blood of patients, then they are concentrated, and the chromatographic allocation of MX is carried out with a subsequent spectrophotometric determination of its concentration. Despite rather high accuracy of MX determination (a few tens of ng/ml), the specified method is characterized by:

duration of the whole determination process reaching two days, that is caused by the necessity of a special pretreatment of samples (processing of patients blood, extraction and concentration of MX, etc.), application of rather expensive equipment, namely, the high-pressure chromatographs or similar devices, necessity to use the high skilled personnel for realization of the whole cycle of the analysis.

A laboratory method for determination of colored BAS, those "targets" are the double-stranded DNA molecules, that takes into account the interaction of BAS with DNA molecules forming liquid crystals immobilyzed in films (gels) biosensor is known as well [Skuridin S. G., Pozdnyakov V. N., Tokareva L. G., Yevdokimov Yu. M. (1991), Patent of the Russian Federation N 2016888].

This method includes:

formation of the lyotropic liquid-crystalline dispersion of DNA in an aqueous-salt solution containing a neutral polymer, addition the special monomers capable to be polymerized, and polymerization of the obtained mixture, reception of a film (gel) with the form and the size that are convenient for the experimentator, immersing of the film (gel) into an analyzed laboratory solution containing BAS, and exposure of the film in this solution during time that is sufficient for diffusion of BAS into the film and interaction with DNA molecules, registration of a spectrum of circular dichroism (abnormal optical activity) in the region of BAS absorption, determination of the BAS presence by the shape of a band in the spectrum of circular dichroism.

However, the exact determination of BAS concentration and, consequently, the practical opportunities of the specified method for BAS determination are limited by the following factors:

difficulty of creation of films (gels) that are adequate to the certain physico-chemical requirements (neutral in relation to DNA character of a film, its transparency, optical isotropy, etc.), difficulty in the maintenance of constant properties of DNA liquid crystals in a film structure, even during time for diffusion of BAS, significant interval of time, after which the registration becomes possible of an appreciable value of the optical signal arising as a result of diffusion of BAS molecules into a polymeric film and their subsequent interaction with nucleic acid moleculs forming the liquid crystalline dispersion, impossibility for exact determination of the value of the abnormal optical signal in the UV-region of the spectrum (i.e., in the DNA absorption region), that is caused by an unsufficient transparency of films (gels) in this part of the spectrum. Therefore, though the presence of the substance under analisis can be registered, the exact determination of its concentration is extremely difficult, application for registration of the abnormal optical signal of the expensive stationary dichrographs (Jobin-Yvon, Mark III or Mark V; Jasco, Model 710/720) being available, as a rule, only in specialized scientific laboratories. A lack of these devices is not only their high cost but also low speed of registration of the optical signal.

A well known dichrograph of "Jasco" firm (Model J-710/720 Spectropolarimeter, Instruction Manual: Jasco Corporation, 2967-5, Ishikwa-Cho, Hachioji City, Tokyo, Japan (June, 1990)), which can be applied as a device for determination of BAS in an analyzed liquid, comprises installed consistently:

a source of light radiation, a selector forming a light flow of a certain wavelength;

a polarizer forming a linearly polarized light of the specified light flow;

a modulator of polarization transforming the linearly polarized light flow into a circularly polarized light flow with a periodically varied direction of rotation of its polarization vector;

a cell for an analyzed sample;

a photodetector transforming an optical signal generated by components of the sample to be analyzed into the proportional electrical signal;

a synchronous amplifier of the specified electrical signal;

a processing unit for processing the received electrical signal and for calculation of the biologically active substance concentration;

a control module.

The specified dichrograph comprises as a selector a low light transmittance double-prism monochromator based on synchronous rotation of two half-prisms by means of an electromechanical driver containing a lever mechanism actuated with an electric motor. The light from a source of light radiation passes trough the double-prism monochromator, those two prisms are tuned on the certain wavelength. The presence of the lever mechanism enables to tune the specified monochromator on different wavelengths of the light flow leaving the monochromator.

However, because of high inertia of the specified driver containing the lever mechanism, the specified selector has a small speed of wavelength tuning. As a result, the usage of the specified dichrograph for BAS determination significantly increases the time of the sample analysis. This factor, at the analyses of biological liquids such as the blood, the urea, etc., can be accompanied by a damage in the health, and in some cases—in the life of patients.

Moreover, because of complex design, the monochromator has large losses on its optical elements, therefore it has a low light transmittance that results in the deterioration of sensitivity of the device as a whole and does not permit to determine low BAS concentrations in analyzed liquids. In addition, the specified device is multifunctional as well, has large dimensions and weight, that requires a specially equipped room for its installation and exploitation. As the result, the specified device has a low mobility and cannot be used for the urgent analyses in clinic laboratories or directly in hospital wards.

The factors named above make fast obtaining the information about the BAS concentration in analyzed liquids difficult and limit wide application of optical systems for such kind of analyses in conditions of clinics and laboratories.

BRIEF SUMMARY OF THE INVENTION

The problem is used as a basis for the offered invention to create a method of determination of BAS in an analyzed liquid with such conditions of its realization and such a device that would allow fastly and precisely to determine the concentrations (low, in particular) of a biologically active substance capable to interact with linear double-stranded DNA molecules in any liquids including biological ones, such as blood plasma, full blood, etc.

This problem is solved by the creation of the method for determination in an analyzed liquid of a biologically active substance interacting with a cholesteric lyotropic liquid-crystalline DNA dispersion formed in a polymer neutral in relation to the DNA, and in this method, according to the invention, the cholesteric lyotropic liquid-crystalline dispersion is formed of the linear double-stranded DNA molecules of low molecular mass immediately before its mixing with an analyzed liquid containing the determined biologically active substance, in addition this analyzed liquid is mixed previously with the specified polymer under conditions, at which optical properties of the lyotropic liquid-crystalline DNA dispersion are not broken, then through the analysed sample obtained as the result of the indicated mixing of the prepared analyzed liquid with the specified liquid-crystalline DNA dispersion, a flow of circularly polarized light is passed, and the optical signal generated by the liquid-crystalline dispersion is registered at two wavelengths, one of them is in the region of the DNA nitrogen bases absorption, and another one is in the region of absorption of the determined biologically active substance, after this a ratio between these signals at the specified wavelengths is calculated, and the concentration of the biologically active substance is determined on this ratio magnitude using the calibration curve.

DETAILED DESCRIPTION OF THE INVENTION

The theory of forming DNA liquid-crystalline dispersions in polimer solutions neutral in relation to this macromolecule is described in [Yevdokimov Yu. M., Skuridin S. G., Salyanov V. I., 1988, Liquid Crystals, 3, p.p.1443–1459], and experimental "boundary" conditions, at which the abnormal optical activity of DNA liquid-crystalline dispersions is preserved, are done in [Evdokimov Yu. M., Skuridin S. G., Akimenko N. M., 1984, Russian Journal: Vysokomolekulyarnye coedineniy, A24, p.2403–2410]. Use of the offered method allows quickly, simply, precisely and with a high accuracy and sensitivity to determine any biologically active substances capable to interact with linear double-stranded DNA molecules in any liquids where it is possible to create the conditions for conservation of the liquid-crystalline DNA dispersions; in addition, it is possible to carry out the analysis in any laboratories where the specially organized rooms and the special qualification of the technicians are not required.

The offered way is especially important for fast, precise and high sensitive determination of the presence and the concentration (including low) of biologically active substances (antitumor compounds, antibiotics, proteins, etc.) in blood of patients in the practice of oncology, surgery, gynecology, at medico-ecological screening, and it helps to rescue of health and life of patients when other methods are inapplicable or do not give the proper results. It is expedient as a neutral polymer to use the polyethyleneglycol, because this polymer is harmless for an experimentator, chemically neutral in relation to DNA, has a high solubility necessary for creation of conditions of the DNA phase exclusion, the optical isotropy and high transparency necessary for measurement of spectra of circular dichroism; moreover, different molecular mass preparations of this polymer of the reasonable price are available.

It is desirable as an analyzed liquid to use the biological liquid because the pharmaco-kinetics of biologically active substances is aimed for application in such liquids as blood, urea, etc.

It is favorable as a biological liquid to use the plasma of blood because a number of the factors influencing accuracy of determination of a biologically active substance decreases in this case.

It is expedient that the biologically active substance should represent an antitumor compound of the anthraquinon group because these compounds are widely used separately as well as in various combinations for chemotherapy of oncological diseases.

It is desirable that the antitumor compound of the anthraquinone group would represent the mithoxantrone because the mithoxantrone is one of the most powerful antitumor agent of a wide spectrum of action.

It is favorable that at determination of the biologically active substance in a biological liquid with heterogeneous in it distribution of the biologically active substance its concentration obtained using the calibration curve should be corrected in view of the coefficient of its distribution between components in a biological liquid.

Thus, the offered method can be used for the fast, precision and high sensitive determination of the presence and the concentration of various biologically active substances (antitumor preparations, antibiotics, proteins, etc.) in various liquids including the blood of patients in the practice of oncology, surgery, gynecology, at medico-ecological screening and at the help to rescue of health and life of patients when other techniques are inapplicable or do not give the proper effect.

The problem presented is solved also by creation of the device for determination of a biologically active substance in an analyzed liquid, comprising installed consistently: a source of light radiation; a selector having at least one optical element and forming a light flow of a certain wavelength; a polarizer forming a linearly polarized light of the pointed light flow; a modulator of polarization transforming the linearly polarized light into a circularly polarized light flow with a periodic change of the direction of rotation of its polarization vector; a cell for the analized sample; a photodetector transforming the optical signal generated by components of the sample into the proportional electrical signal; a synchronous amplifier increasing the pointed electrical signal; a processing unit for processing the obtained electrical signal and for calculation of the biologically active substance concentration; a control module, and in this device, according to the invention, the selector contains an electrodynamic driver of a positional type, designed with a possibility of setting at least two wavelengths, at which the optical signal generated by the components of the sample under analysis is registered, and at least one optical element fixed on a motor shaft of the specified driver.

The presence of the specified driver and the optical element fixed on its motor shaft allows quickly and precisely to set the required wavelengths and to tune the device from one wavelength to another one, that allows to reduce a time period for the selection of the required wavelength by ten, at least, with simultaneous decreasing an electric power consumption; it allows quickly, precisely and with a high sensitivity to determine the concentration (including low) of biologically active substances capable to interact with the double-stranded DNA molecules in the analyzed liquids including the biological liquids, such as full blood, plasma of blood, etc.

It is expedient that the selector should represent a simple monochromator containing at least two optical elements, one of them represents a dispersive element, and one of these optical elements is fixed on the motor shaft of the specified driver with the possibility to turn around its own axis. In addition the dispersive element can represent a diffraction grating that can be designed concave.

It is possible that the selector should represent a simple monochromator containing one optical element fixed on the motor shaft of the specified driver with the possibility to turn around its own axis, and this optical element must be the dispersive element designed as the concave diffraction grating.

The presence of the simple monochromator with minimal number of optical elements simplify a design of the device as a whole that allows considerably to reduce its dimensions. It results in significant cheapening of the device and allows to equip with this device any laboratories, as the offered device does not require a presence of specially organized place and special qualification of the personel. Moreover, the usage of the simple monochromator allows to simplify the optical system of the device, to reduce losses of light on optical elements, that is to increase a light flow transmittance, and, due to this, to increase the sensitivity of the device, to reduce its size and, hence, to ensure the mobility of the device for its use under any conditions. Use of the diffraction grating as the dispersive element gives a possibility to keep the required resolving force of the monochromator, so not to lose in the spectral resolution of the selector.

It is possible that the selector should contain a grate number of optical elements being a set of narrow-band interference filters fixed on the motor shaft of the specified driver with a possibility of their alternate introduction into the light flow, in addition each of these filters has a transparency band in the region of the certain wavelength chosen for the concrete biologically active substance.

The usage in the selector of a set of the interference filters fixed on the motor shaft of the electrodynamic driver of the positional type allows, at maintenance of a high speed of the selection of the required wavelength, essentially to simplify the optical scheme of the selector and, hence, to increase the transmittance of the light flow and to reduce the dimensions and the weight of the whole device.

It is expedient that the electrodynamic (galvanometric) driver should contain a motor having both a stator and a rotor, and the rotor turn angle transducer, representing an inductive differential converter of the rotor turn angle into the electrical signal, and containing a modulator that is designed as a ring fixed on the motor shaft with an eccentricity concerning its rotation axis.

Due to the presence of the specified eccentricity there is a possibility to realize the required character of the dependence of the signal amplitude of the turn angle transducer, i.e. the wavelength of the selector, upon the turn angle of the motor shaft, and the character of this dependence is determined by the form (design) of the modulator.

Thus, the usage of the offered method and the offered device allows quickly, precisely and with a high sensitivity to determine the presence and the concentration of various biologically active substances (antitumor compounds, antibiotics, proteins, etc.) in various liquids including biological liquids, for example, in blood of patients, in practice of oncology, surgery, gynecology, at the abnormal optical activity of the sample is measured at two wavelengths, one of them is in the region of absorption of DNA nitrogen bases, and another one is in the region of BAS absorption. (The band in the region of the DNA absorption is used as the internal standard for the "quality" of the liquid-crystalline dispersions formed, and also reflects the stability and the correctness of action of the offered device; the band in the spectrum of circular dichroism in the region of BAS absorption represents by itself as the indicator of the BAS presence in the analysed sample, and the amplitude of this band reflects the concentration of the BAS), the ratio is calculated between the values of the optical signals at wavelengths indicated above, the exact BAS concentration is determined due to the calibration curve that reflects the dependence of values of the signals ratio upon the BAS concentrations and is previously constructed according to the method described above.

For the best understanding of the present invention, a few examples describing various stages of the declared method, with the references to the applied drawings is given below. Here:

FIG. 1 characterizes the spectrum of absorption of the initial aqueous-salt solution of the linear double-stranded DNA used for formation of particles of the cholesteric liquid-crystalline dispersions, in coordinates: "optical density, A"—"λ, wavelength";

$C_{DNA}$~80 µg/ml;

Chicken erythrocyte DNA ("Reanal", Hungary);

Mol.mass of DNA~(3–5)×10$^5$ Da.

FIG. 2 characterizes the circular dichroism spectra of the initial DNA and its cholesteric liquid-crystalline dispersion in coordinates: "Δε=$ε_L$-$ε_R$"—"λ, wavelength", where:

value of Δε=ΔA/$C_{DNA}$—the molar circular dichroism;

$ε_L$—the dichroism for the left-circular-polarized light; presence in the analysed sample, and the amplitude of this band reflects the concentration of the BAS), the ratio is calculated between the values of the optical signals at wavelengths indicated above, the exact BAS concentration is determined due to the calibration curve that reflects the dependence of values of the signals ratio upon the BAS concentrations and is previously constructed according to the method described above.

BRIEF DESCRIPTION OF DRAWINGS

For the best understanding of the present invention, a few examples describing various stages of the declared method, with the references to the applied drawings is given below. Here.

value of Δε=ΔA/$C_{DNA}$—the molar circular dichroism;

$ε_L$—the dichroism for the left-circular-polarized light;

$ε_R$—the dichroism for the right-circular-polarized light;

ΔA—the experimentally measured circular dichroism, $C_{DNA}$—the DNA concentration;

the curve 1—the CD spectrum of the cholesteric liquid-crystalline DNA dispersion;

the curve 2—the CD spectrum of the aqueous-salt solution of the initial linear DNA;

The curve 1 (right ordinate): $C_{PEG}$=170 mg/ml, PEG mol. mass=4000 ("Ferak", Germany); 0.3 M NaCl+10$^{-2}$ M phosphate buffer; pH~7.0.

The curve 2 (left ordinate): 0.3 M NaCl+10$^{-2}$ M phosphate buffer; pH~7.0.

Figure 3:
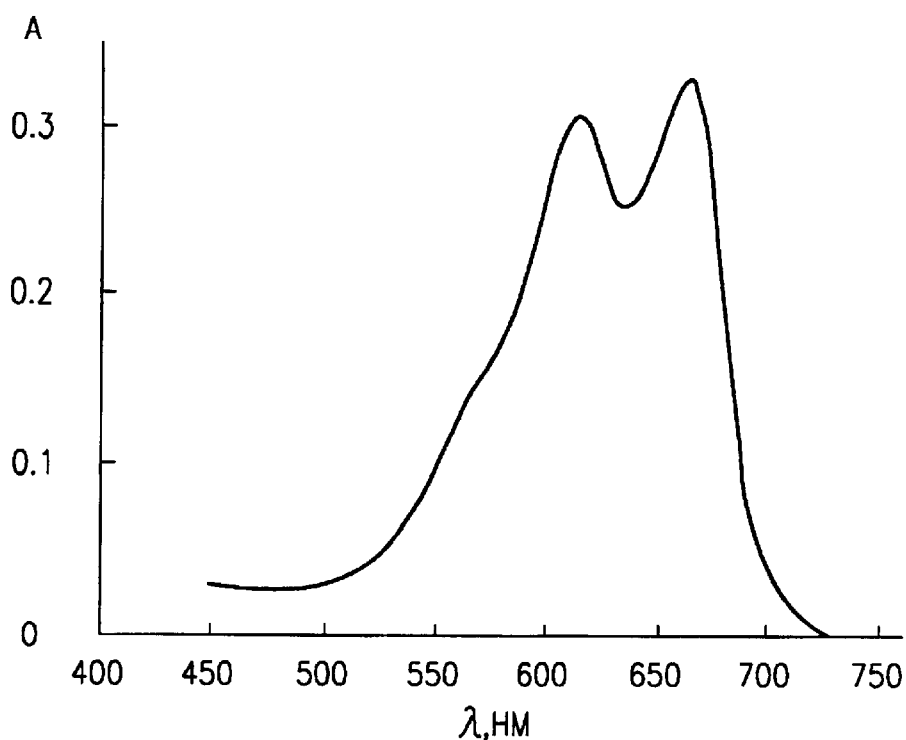

FIG. 3 characterizes the absorption spectrum of the mithoxantrone used as an example of BAS, in coordinates: "optical density, circular dichroism A"—"wavelength, λ";

0.3 M NaCl+10$^{-2}$ Ml phosphate buffer; pH~7.0; $C_{t\ MX}$=1.5×10$^{-5}$ M.

Figure 4:
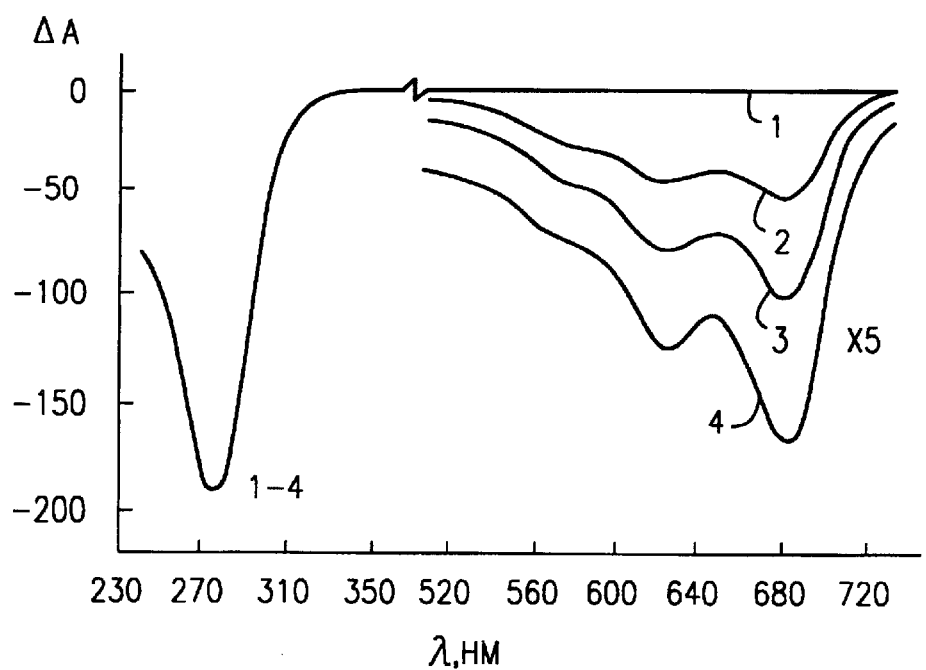

FIG. 4 characterizes the circular dichroism spectra of the liquid-crystalline DNA dispersion treated with different concentration of the mithoxantrone, in coordinates: "circular dichroism ΔA=$A_L$-$A_R$"—"wavelength, λ", where:

$A_L$—the dichroism for the left-circularly polarized light;

$A_R$—the dichroism for the right-circularly polarized light;

ΔA—the experimentally measured circular dichroism,

1-$C_{t\ MX}$=0; 2-$C_{t\ MX}$=1.55×10-6 M;

3-$C_{t\ MX}$=3.08×10$^{-6}$ M; 4-$C_{t\ MX}$=5.35×10$^{-6}$ M;

$C_{DNA}$=20 µg/ml; $C_{PEG}$ _170 mg/ml;

0.3 M NaCl+10$^{-2}$ M phosphate buffer; pH~7.0;

"ΔA=$A_L$-$A_R$" is in mm; 1 mm=5×10$^{-5}$optical units; L=1 cm.

Figure 5:
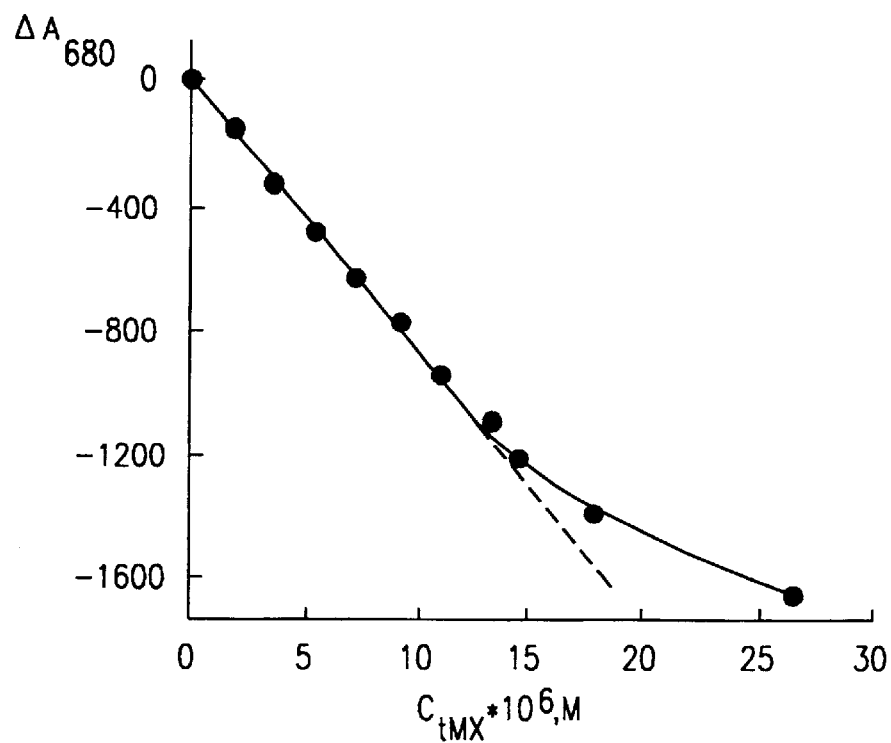

FIG. 5 reflects the dependence of the amplitude (Δ$A_{680}$) of the negative band at λ=680 nm in the circular dichroism spectrum of the liquid-crystalline DNA dispersion upon the concentration ($C_{t\ MX}$) of the mithoxantrone added; the arrow in the Fig. designates the mithoxantrone concentration, down to which between values of Δ$A_{680}$ and $C_{t\ MX}$ directly proportional dependence is observed;

$C_{DNA}$=20 µg/ml; $C_{PEG}$=170 mg/ml;

0.3 M NaCl+10$^{-2}$ M phosphate buffer; pH~7.0

Δ$A_{680}$ is in mm; 1 mm=1×10$^{-6}$ optical units; L=1 cm.

Figure 6:
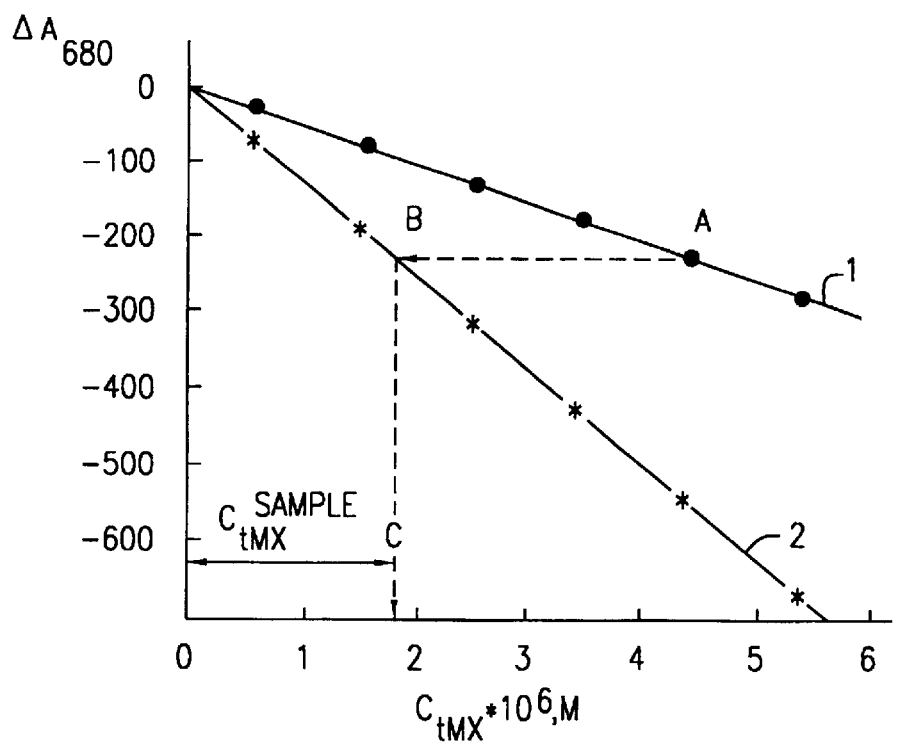

FIG. 6 shows the dependence of the amplitude of the band in the circular dichroism spectra of the liquid-crystalline dispersions of the (DNA-MX) complexes at λ=680 nm upon the value $C_{t\ MX}$ in the analyzed samples and in the control solutions (1 and 2, respectively). In FIG. 6 (A→B→C=$C_{t\ MX}$) the way for determination of $C_{t\ MX}$ in the analyzed sample is shown that takes into account the binding of the mithoxantrone with form elements of blood and high-molecular components of plasma of different chemical nature;

$C_{DNA}$=20 µg/ml; $C_{PEG}$=170 mg/ml;

0.225 M NaCl+7.5×10$^{-3}$ M phosphate buffer; pH~7.0.

Δ$A_{680}$ is in mm; 1 mm=2×10$^{-6}$ optical units; L=1 cm.

Figure 7:
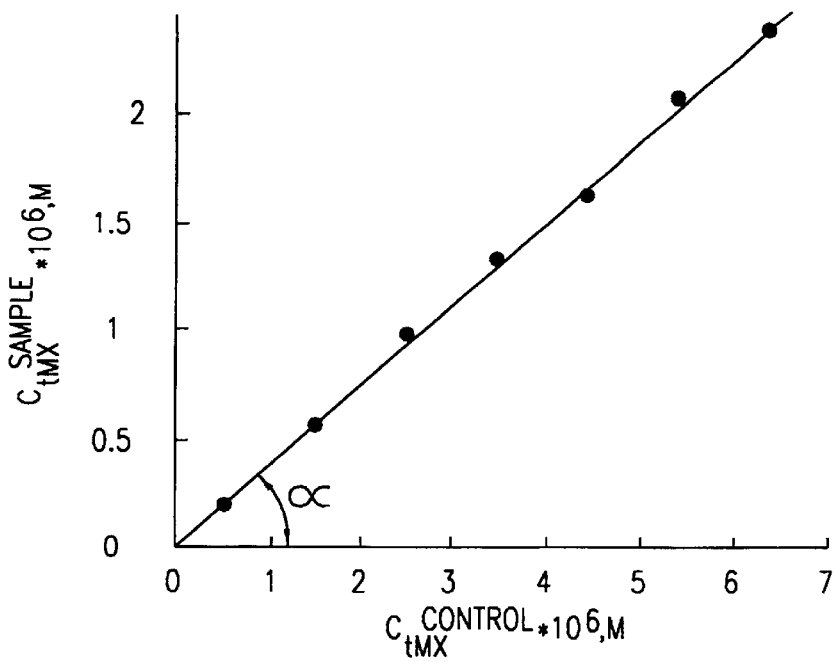

FIG. 7 reflects the dependence of the $C_{t\ MX}^{sample}$ magnitude on the $C_{tMX}^{control}$ value;

$C_{DNA}$=20 µg/ml; $C_{PEG}$=170 mg/ml;

0.225 M NaCl+7.5×10$^{-3}$ M phosphate buffer; pH~7.0.

Figure 8:
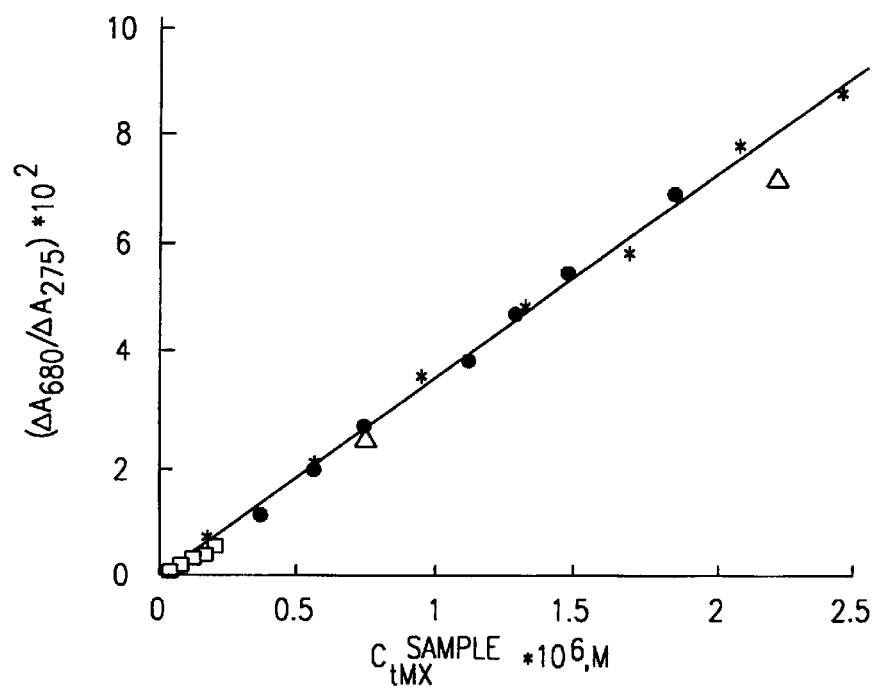

FIG. 8. shows the dependence of the ratio of the bands in the CD spectra of the liquid-crystalline dispersions of the (DNA-MX) complexes at $\lambda_1$=680 nm and $\lambda_2$=275 nm upon the $C_{t\,Mx}^{sample}$ value. In FIG. 8 the different points concern to experiments carried out with the use of blood of four different donors;

$C_{DNA}$=20 µg/ml; $C_{PEG}$=170 mg/ml;

0.225 M NaCl+7.5×10$^{-3}$ M phosphate buffer; pH~7.0.

$\Delta A_{680}$ and $\Delta A_{275}$ are in mm; 1 mm=2×10$^{-6}$ optical units; L=1 cm.

Figure 9:
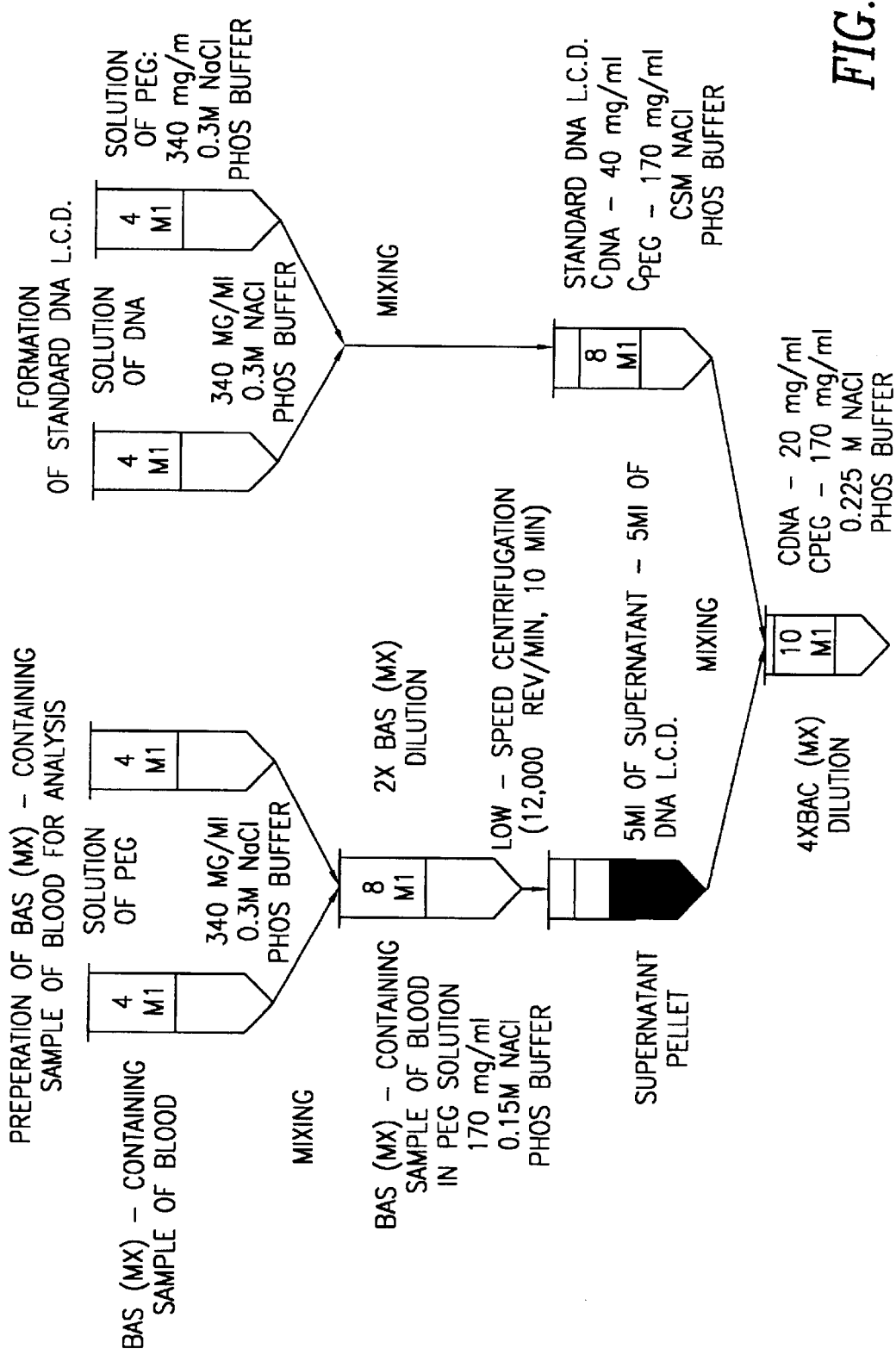

FIG. 9. represents the basic scheme of stages for preparation of an analysed sample of blood for determination of the presence of a BAS interacting with the liquid-crystallinr DNA dispersion. (It is necessary to pay attention on the fact resulted from the offered method of blood preparation that the initial BAS concentration decreases by four).

Figure 10:
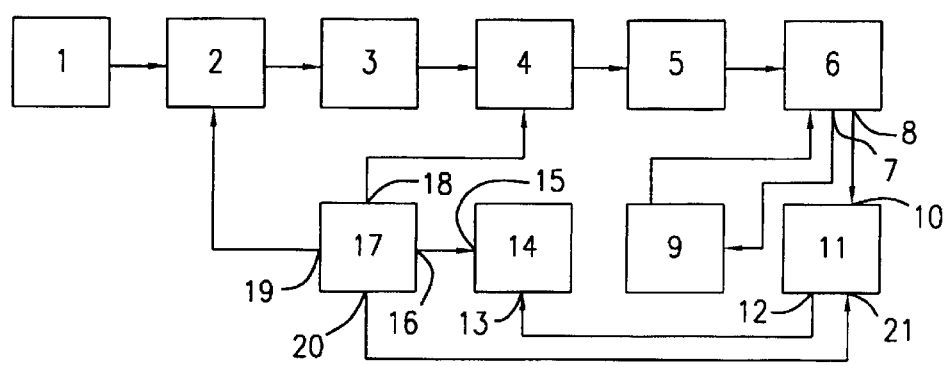
Figure 11:
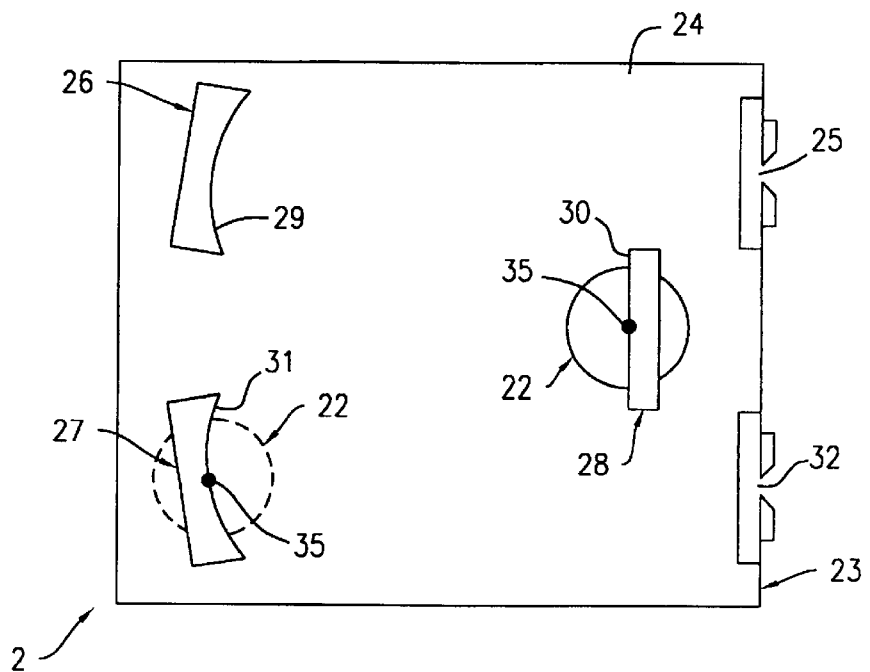
Figure 12:
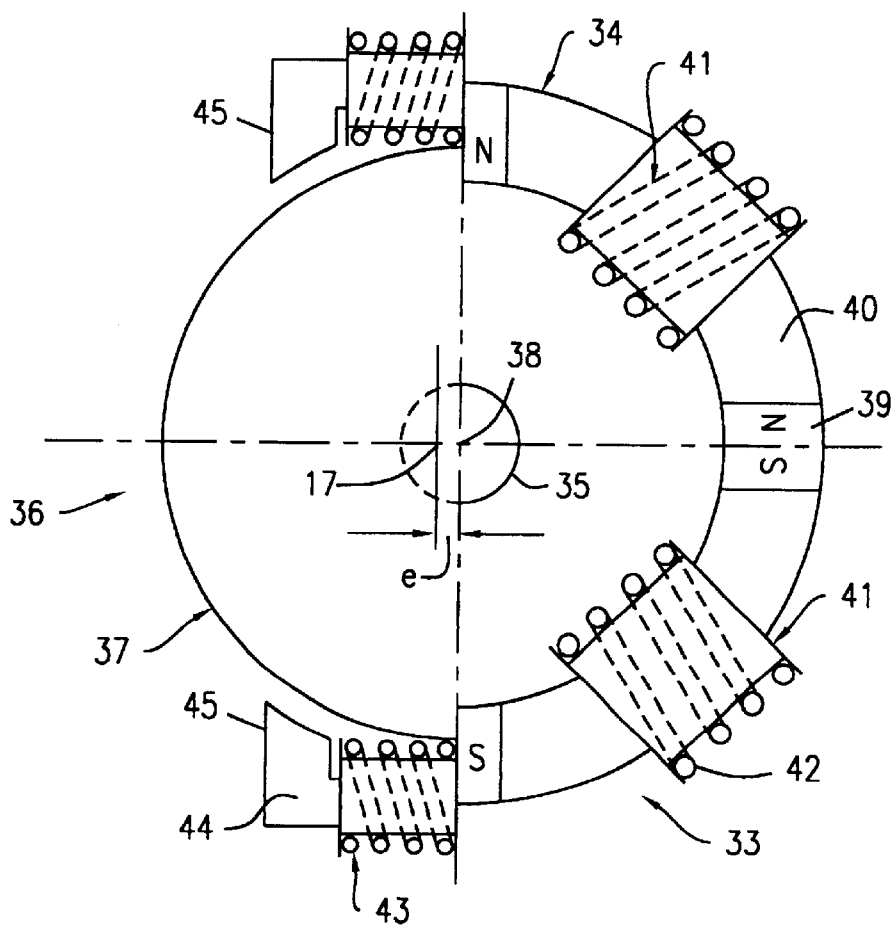
Figure 13:
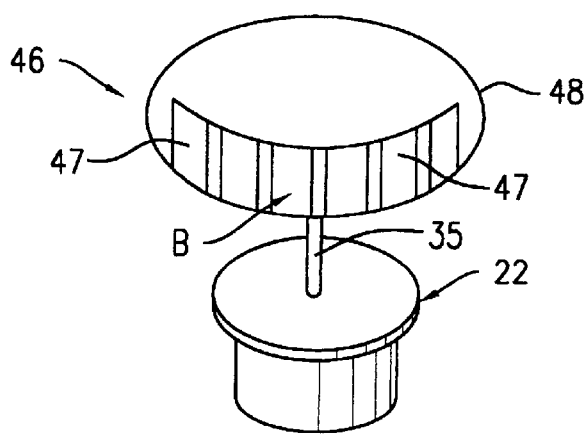
Figure 14:
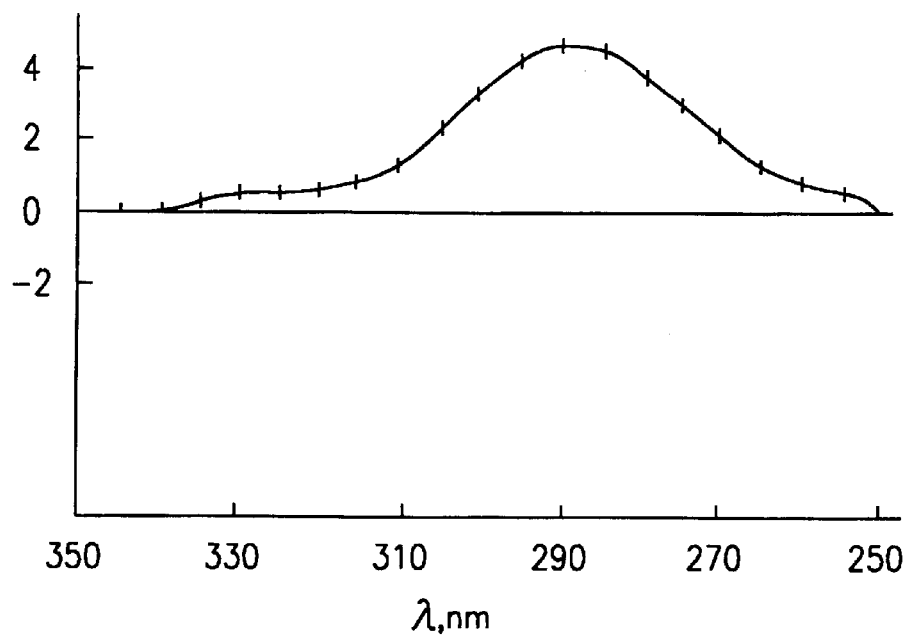

FIG. 10 represents the block diagram of the device designed according to the invention;

FIG. 11 schematically shows the selector representing a simple monochromator designed according to the invention, top view;

FIG. 12 schematically represents the electrodynamic driver of the positional type designed according to the invention, top view with the complex section;

FIG. 13 schematically shows the selector representing a set of interference filters that is designed according to the invention, isometry;

FIG. 14—the CD spectrum of the aqueous-salt solution of n-propylammonium salt of d-10-camphorsulphonic acid registered by the offered device;

$C_{10}H_{16}O_4S$ concentration 0.15 mg/ml;

wavelength scan step=5 nm/div.

Figure 15:
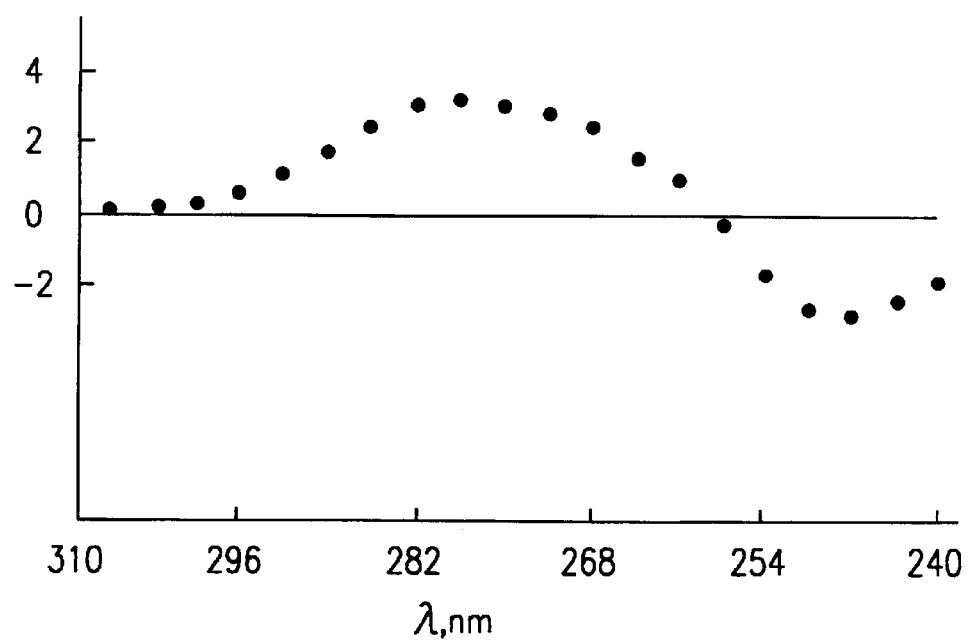

FIG. 15—the CD spectrum of the aqueous-salt solution of the linear B-form DNA registered by the offered device;

$C_{DNA}$=5 µg/ml; 0.3 M NaCl+10$^{-2}$ M phosphate buffer; pH~7.0;

wavelength scan step=3.5 nm/div.

Figure 16:
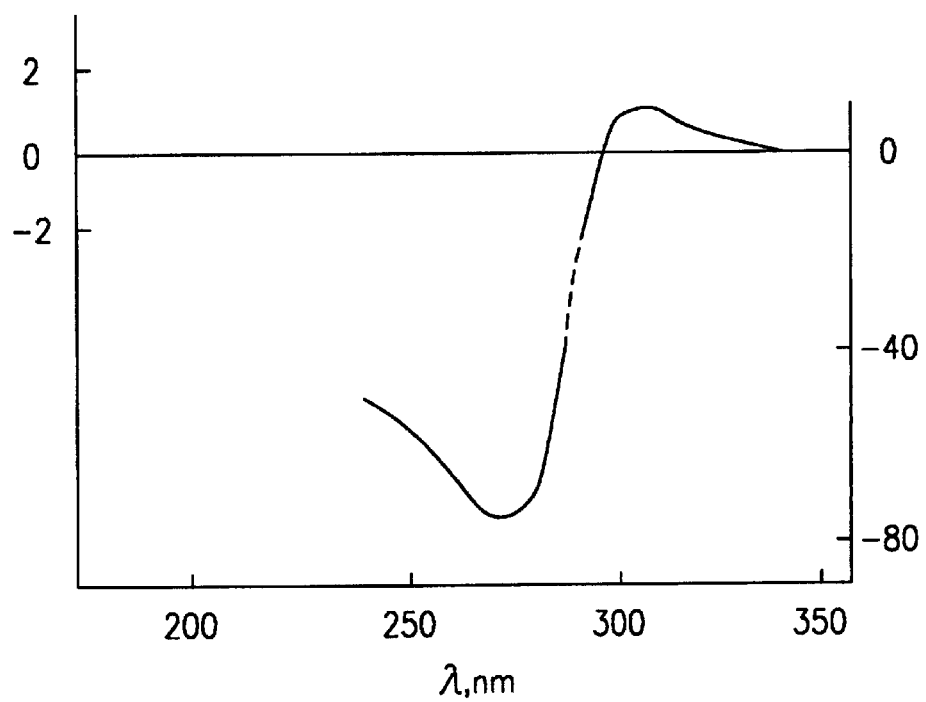

FIG. 16—the CD spectrum of the liquid-crystalline DNA dispersion registered by the portable dichrometer;

$C_{DNA}$=5 µg/ml; $C_{PEG}$=170 mg/ml;

0.3 M NaCl+10$^{-2}$ M phosphate buffer; pH~7.0;

wavelength scan step=10 nm/div.

Figure 17:
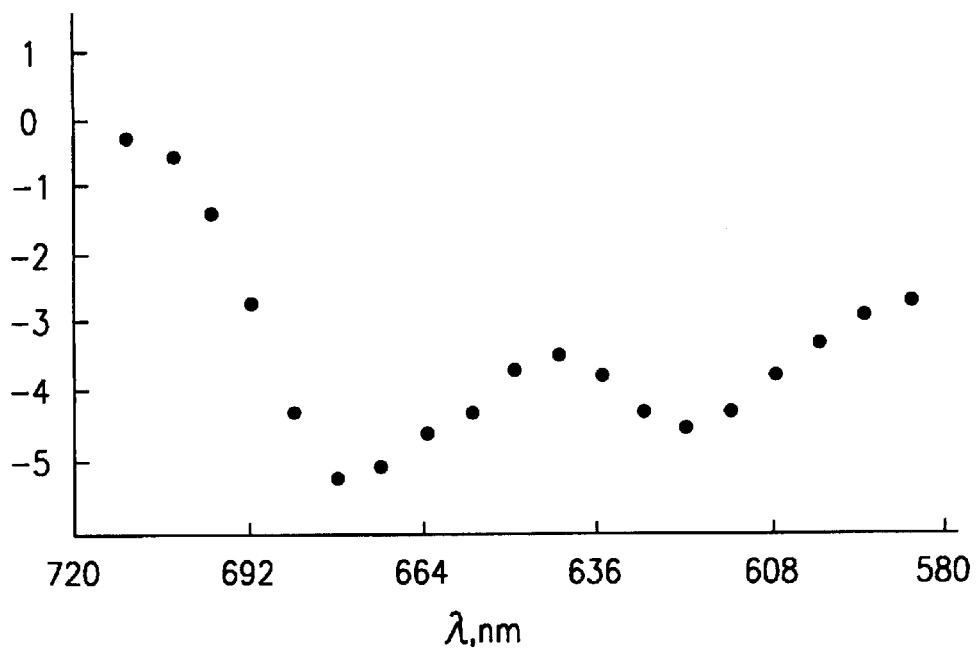

FIG. 17—the CD spectrum of the liquid-crystalline dispersion of the complex (DNA-MX) registered with help of the portable dichrometer;

$C_{DNA}$=5 µg/ml; $C_{PEG}$=170 mg/ml;

0.3 M NaCl+10$^{-2}$ M phosphate buffer; pH~7.0;

$C_{t\,MX}$=8.623×10$^{-7}$ M.

wavelength scan step=7 nm/div.

Figure 18:
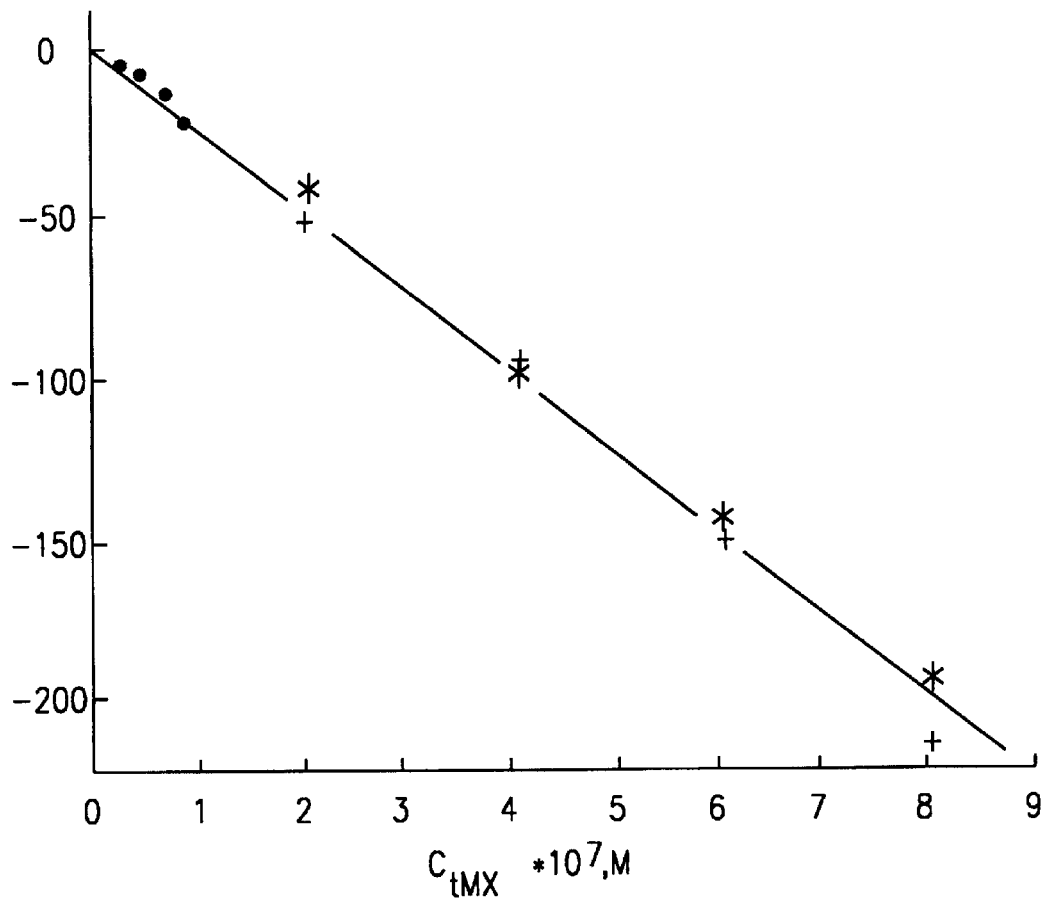

FIG. 18—the dependence of the optical signal generated by the liquid-crystalline DNA ($\lambda$=680 nm) upon the total concentration of MX. The various black points designate the data received by the portable dichrometer in different series that are distinguished by MX concentration.

EXAMPLE 1

Forming the Liquid-Crystalline DNA Dispersion 1.1. Probes of NaCl (17.532 g), NaH$_2$PO$_4$×2 H$_2$O (0.78 g) and Na$_2$HPO$_4$×12H$_2$O (1.79 g) are placed into a calibrated flask (V =1000 ml) and dissolved in distillated water; water is added up to a label.

By such a way 1 L of 0.3 M of NaCl solution containing 10$^{-2}$ M of phosphate buffer is prepared.

1.2. 10 mg of the double-stranded DNA preparation ("Reanal", Hungary; molecular mass (0.3–0.5)×10$^5$ Da) are placed into a calibrated flask (V=10 ml) and dissolved in the solution prepared according to item 1.1. The volume of the solution is added up to a label.

By such a way 10 ml of aqueous-salt solution of the DNA with its fixed concentration are prepared. The DNA concentration is determined using a spectrophotometer and being derived from the ratio: 1 mg of the DNA corresponds to 20 optical units in 1 ml ($\lambda_{max}$=258.4 nm; pH~7.0).

1.3. Probes of NaH$_2$PO$_4$×2H$_2$O (0.078 g) and Na$_2$HPO$_4$× 12H$_2$O (0.179 g), NaCl (1.7532 g) and polyethyleneglycol (PEG) ("Ferak", Germany; PEG molecular mass 4000; 34 g) are placed into a calibrated flask (V=100 ml) and dissolved in distillated water; water is added up to a label.

By such a way 100 ml of aqueous-salt solution of PEG ($C_{PEG}$=340 mg/ml; 0.3 M NaCl+10$^{-2}$ M phosphate buffer) are prepared.

1.4. 4.6 ml of the solution 1.1 are mixed with 0.4 ml of the solution 1.2 in a glass test-tube (V=10 ml).

By such a way 5 ml of aqueous-salt solution of the double-stranded linear DNA are prepared ($C_{DNA}$=80 µg/ml; 0.3 M NaCl+10$^{-2}$ M phosphate buffer).

Figure 1:
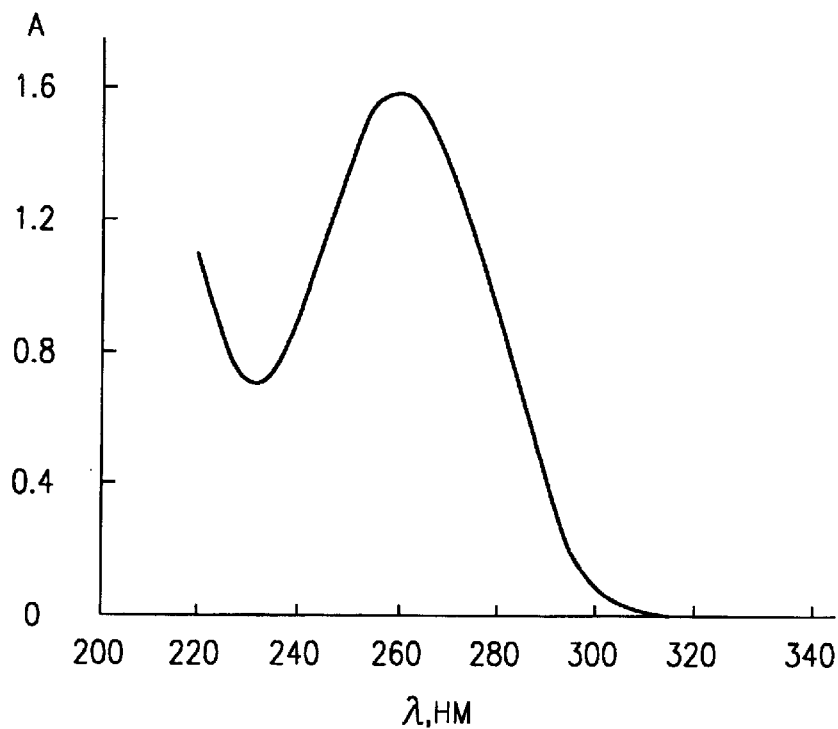
FIG. 1 characterizes the spectrum of absorption of the initial aqueous-salt solution of the linear double-stranded DNA used for formation of particles of the cholesteric liquid-crystalline dispersions, in coordinates: "optical density, A"—"λ-wavelength"; $C_{DNA}$~80 µg/ml; Chicken erythrocyte DNA ("Reanal", Hungary); Mol.mass of DNA~(3–5)×10$^5$ Da.

After mixing solutions 1.1 and 1.2 the absorption spectrum is registered of aqueous-salt solution of the given DNA concentration prepared according to item 1.4 (FIG. 1, where the absorption spectrum of the DNA aqueous-salt solution is represented, $C_{DNA}$~80 mkg/ml; DNA of chicken erythrocytes ("Reanal", Hungary); DNA mol. Mass~(3–5)×10$^5$ Da).

1.5. 4 ml of the solution 1.3 are mixed with 4 ml of the solution 1.4 in a glass test-tube (V=15 ml); the mixture obtained is intensively mixed during 3 min.

By such a way 8 ml of the liquid-crystal DNA dispersion ($C_{DNA}$=40 µg/ml; $C_{PEG}$=170 mg/ml; 0.3 M NaCl+10$^{-2}$ M phosphate buffer).

Figure 2:
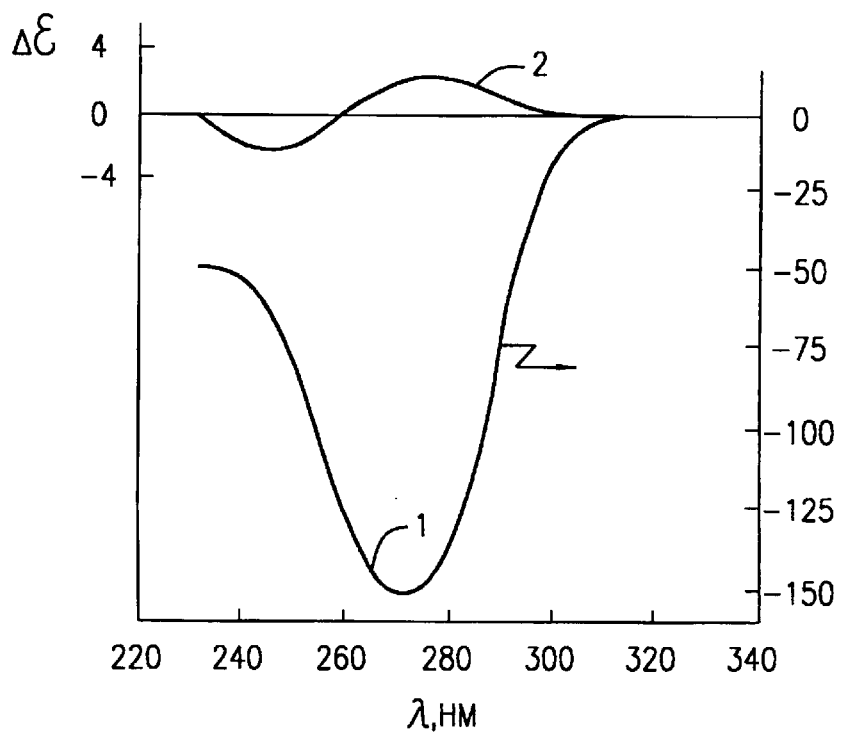
FIG. 2 characterizes the circular dichroism spectra of the initial DNA and its cholesteric liquid-crystalline dispersion in coordinates: "Δε=$ε_L$-$ε_R$"—"λ-wavelength", where.

After mixing, the circular dichroism (CD) spectrum is registered of the mixture prepared on item 1.5. The intense negative band in the region of absorption of the DNA nitrogen bases (FIG. 2, curve 1) testifies that, as a result of mixing solutions prepared on items 1.3 and 1.4, the liquid-crystalline DNA dispersion of the cholesteric type is formed.

EXAMPLE 2

Optical Properties of the Liquid-Crystalline DNA Dispersion Treated with Mithoxantrone 2.1. A probe 0.4 mg of mithoxantrone (MX; the antitumor substance of the anthraquinone group) is placed into a test-tube (V =0.5 ml) and dissolved in 200 µl of the solution 1.1.

By such a way 200 µl of the MX aqueous-salt solution ($C_{MX}$=2 mg/ml; 0.3 M NaCl+10$^{-2}$ M phosphate buffer) are prepared.

2.2. The MX concentration in the solution 2.1 is determined by specrophotometer ("Specord" M 40, Germany), using the known meaning of MX molar extinction coefficient ($\epsilon$=21500 M$^{-1}$ cm$^{-1}$; $\lambda_{max}$=660 nm). The molar MX concentration in the solution 2.2 is 3.868×10$^{-3}$ M.

In FIG. 3 the absorption spectrum of the MX aqueous-salt solution is shown.

2.2. 2 ml of the standard liquid-crystalline DNA dispersion prepared on item 1.5 are placed into a rectangular optical quartz cell (V=4 ml; optical length=1 cm), and its CD spectrum is registered in the wavelength region 750–220 nm by a dichrograph "Jobin-Yvon, Mark III" (France).

2.3. 1 μl portions of the solution 2.1 (total volume of the added solution 2.1 is 6 μl) are put into the cell containing 2 ml of the DNA dispersion prepared on item 2.2; after each portion of the solution 2.1, the solution in the optical cell is mixed, and the CD spectrum is registered in the wavelength region 750–220 nm.

In FIG. 4 the CD spectrum of the initial liquid-crystalline DNA dispersion (the curve 1) is compared to that of the same dispersion added with different MX concentrations $C_{t\ MX}$ ($C_{t\ MX}$—the total concentration of MX added in the solution of the liquid-crystalline DNA dispersion). The MX addition is accompanied by an appearance of an additional intense negative band in the region of MX absorption (680 nm) in the CD spectrum of the liquid-crystalline DNA dispersion. In addition, the amplitude of the band at the wavelength λ=680 nm "is connected" to the amplitude of the band at λ=275 nm in a following way: at identical concentration of MX if the amplitude of the 680 nm band is larger, then the amplitude of the λ=275 nm band is higher, and on the contrary.

The dependence of the amplitude of the band at λ=680 nm in the CD spectrum of the liquid-crystalline dispersion of complexes (DNA-MX) upon Ct MX (FIG. 5) shows that between the value of AA at 680 nm and $C_{t\ MX}$ directly proportional dependence is observed in the range of MX concentrations from 0 down to $12 \times 10^{-6}$ M. As the amplitude of the band in the CD spectrum in the region of MX absorption ($\Delta A_{680}$) depends only on the concentration of MX molecules bound ($C_{b\ MX}$) in a complex with the DNA molecules, and as between values of $C_{t\ MX}$ and $C_{b\ MX}$ there is a simple ratio:

$$C_{t\ MX} = C_{b\ MX} + C_{free\ MX} \qquad (1)$$

where: $C_{free\ MX}$—concentration in the solution of free (unbound in a complex with the DNA) MX molecules, one can consider directly proportional dependence between values $\Delta A_{680}$ and $C_{t\ MX}$ as the indication to a low concentration of free MX in the solution.

The value of $C_{b\ MX}$, at the fixed DNA concentration, is closer to the $C_{t\ MX}$ value, then the last concentration is lower. In the area of the pharmaceutically relevant meanings of MX concentrations (ng/ml), one can accept that the value of $C_{b\ MX}$ is approximately equal to the value of $C_{t\ MX}$.

Thus, the intense band in the region of MX absorption in the CD spectrum in combination with the presence of the directly proportional dependence of the amplitude of this band on the concentration of MX added can be used for determination of the MX presence and concentration.

At determination of the concentration of MX molecules that can interact with DNA molecules, and, hence, of the MX concentration in biological liquids by the circular dichroism spectra, it is necessary to take into account that this determined value could be influenced by two factors:
1) Distribution of MX molecules between form elements of blood,
2) "Heterogeneity" of optical properties of the liquid-crystalline DNA dispersions in blood of different patients, influencing the amplitude of the band at λ=275 nm, and, hence, the amplitude of the band at λ=680 nm.

Therefore for the accurate determination of the MX concentration it is necessary to take into account the influence of these factors.

EXAMPLE 3

Consideration of Mithoxantrone Distribution in Blood of Patients

At determination of MX concentration in biological liquids (blood, blood plasma, etc.) it is necessary to take into account a possible binging of MX coming in blood with form elements of blood and different origin high-molecular components of blood plasma. An example below allows to estimate a degree of MX binding.

3.1. Blood probes (in 2 ml) are spilled into 8 centrifuge polypropylene test-tubes (V=12.5 ml).

3.2. 0, 1, 3, 5, 7, 9, 11 and 13 μl of the solution prepared on item 2.1. are added correspondingly in each of test-tubes (item 3.1).

3.3. After addition of the solution 2.1 on the blood probes each of the prepared probes is mixed.

By such a way a series of MX-containing samples of blood in which $C_{t\ MX}$ varies from 0 down to $24.98 \times 10^{-6}$ M is prepared.

3.4. In 2 ml of the solution prepared on item 1.3 are added on each of MX-containing blood samples prepared according to items 3.1–3.3.

3.5. After addition of the solution 1.3 on blood samples (item 3.3) the prepared solutions are mixed.

By such a way MX-containing blood samles in the PEG aqueous-salt solution ($C_{t\ MX}$ from 0 down to $12.49 \times 10^{-6}$ M; $C_{PEG}$=170 mg/ml; 0.15 M NaCl+$5 \times 10^{-3}$ M phosphate buffer) are prepared.

3.6. The blood samples prepared according to item 3.5 are certrifugated (12,000 rev/min; 4° C.; centrifuge K24D, Germany).

As a result of centrifugation, a deposit consisting of form elements of blood and high-molecular components of blood plasma is formed.

3.7. After low speed centrifugation in 2 ml of the supernatant from each of centrifuge test-tubes (item 3.6; 8 test-tubes) are selected and transfered into 8 corresponding glass test-tubes (V=10 ml).

3.8. In 2 ml of the standard liquid-crystalline DNA dispersion formed according to item 1.5 are added in each of 8 glass test-tubes containing in 2 ml of the supernatant (item 3.7).

3.9. The solutions prepared according to item 3.8 are stirred.

By such a way a series of the analyzed samples is prepared that contain the initial liquid-crystalline DNA dispersion and the supernatant of PEG-containing samples of blood with different MX contents ($C_{DNA}$=20 μg/ml; $C_{PEG}$=170 mg/ml; 0.15 M NaCl+$5 \times 10^{-3}$ M phosphate buffer).

3.10. In parallel with the sample series (item 3.9), a control series of samples according to operations on items 3.1–3.9 is prepared, where, instead of blood, the solution 1.1 is used. (In the control series $C_{t\ MX}$ varies from 0 down to $6.245 \times 10^{-6}$ M).

3.11. After mixing the analyzed samples (item 3.9) and the control solutions (item 3.10) the CD spectra of the analyzed (item 3.9) and the control (item 3.10) sample series are registered with a dichrograph "Jobin-Yvon, Mark III" (France).

The amplitude of the band in the CD spectra (λ=680 nm) of PEG containing samples of blood (item 3.4) grows in accordance with increasing $C_{t\ MX}$ (FIG. 6, curve 1).

Distinction between lines 1 and 2 (FIG. 6) shows that the analyzed blood samples contain smaller, in comparison with the control samples, concentration of MX. The reduction of MX concentration reflects the fact that the part of MX molecules binds to form elements of blood and high-molecular components of plasma and, hence, becomes inaccessible (item 3.6) for determination by means of the optical method.

For consideration of the divergence between the same concentration meanings ($C_{t\ MX}$) of MX added in the blood and in the control solutions, a technique shown in FIG. 6 is used.

According to this technique the amplitude of the band, that is characteristic for the CD spectrum of the analyzed blood sample at $\lambda=680$ nm (line 1, point "A"), is transferred on line 2 (point "B") that represents the dependence of the value of $\Delta A_{680}$ upon $C_{t\ MX}$ for the control series of solutions:

$$A \to B \to C = C_{tMX}^{sample}.$$

The meaning of the value $\Delta A_{680}$ in a point "B" on the absciss axis is corresponded to the value of $C_{t\ MX}$ (point "C"), i.e. the meaning of the MX concentration in the analyzed sample ($C_{t\ MX}^{sample}$)

In FIG. 7 the dependence of the MX concentration in the analyzed blood samples ($C_{tMX}^{sample}$) upon its value in the control solutions ($C_{t\ MX}^{control}$) is presented.

The dependence between these values is described by the straight line with the inclination angle tangent 0.384. It means that under conditions used only 38.4% of total MX molecules added in blood samples remain accessible to the analysis by the optical methods. This value should be entered into the final equation for determination of the concentration of MX added in blood.

EXAMPLE 4

Consideration of Probable "Heterogeneity" of Optical Properties of the Liquid-Crystalline DNA Dispersions at Calculation of MX Concentration in an Analyzed Biological Liquid 4.1. To exclude the "heterogeneity" of optical properties of the liquid-crystalline DNA dispersion in blood of different patients, and, hence, the value of the optical signal generated by these liquid-crystalline dispersions at formation of the (DNA-MX) complex, the meanings of $\Delta A_{680}$ received in experiments on determination of MX were normalized on the value of the optical signal registered in the CD spectrum of the control liquid-crystalline DNA dispersion at $\lambda=275$ nm ($\Delta A_{275}$).

4.2. Dependence of the ratio ($\Delta A_{680}/\Delta A_{275}$) upon the value $C_{t\ MX}^{sample}$ (FIG. 8) received for blood of four different donors represents an universal calibration curve, and using this curve it is possible to determine values of $C_{t\ MX}^{sample}$ in the region of MX concentrations from 0 down to $2.5 \times 10^{-6}$ M.

EXAMPLE 5

The Algorithm for Determination of Concentration of a Biogically Active Substance in Blood of a Patient The preparation of blood taken from a patient and containing a biologically active substance, and the estimation of BAS concentration is carried out according to the scheme shown in FIG. 9. In accordance with this scheme tested on the example of determination of MX concentration:

5.1. 4 ml of blood taken from a patient are mixed In polypropylene centrifuge test-tube (V=12.5 ml) with 4 ml of the solution on item 1.3.

5.2. The prepared mixture is stirred.

By such a way the blood sample is prepared that contains a biologically active substance (BAS) in the PEG aqueous-salt solution.

5.3. The BAS-containing blood sample in the PEG aqueous-salt solution prepared on item 5.2 is centrifugeted.

5.4. After low-speed centrifugation, 5 ml of the supernatant are mixed with 5 ml of the standard liquid-crystalline DNA dispersion prepared on items 1.1–1.5 (example 1).

By such a way the analyzed blood sample is prepared.

5.5. In parallel with preparation of the blood sample, the control liquid-crystalline DNA dispersion is prepared on items 5.1–5.4 where, instead of blood, the solution on item 1.1 is used.

5.6. After mixing the analyzed blood sample (item 5.4) and the control liquid-crystalline DNA dispersion (item 5.5), the amplitudes of the bands in the CD spectra are registered, accordingly, at the wavelength $\lambda_1$ in the region of BAS absorption (in our case—at 680 nm; $\Delta A_{680}$) and at the wavelength $\lambda_2$ that is appropriate to the region of DNA absorption (275 nm; $\Delta A_{275}$).

5.7. The ratio $\Delta A_{680}/\Delta A_{275}$ is calculated.

5.8. The received ratio (item 5.7) is put on the universal calibration curve (FIG. 8, example 4.2), and the meaning of $C_{t\ BAS(MX)}^{sample}$ value that corresponds to this ratio is determined.

5.9. After determing the value of $C_{t\ BAS(MX)}^{sample}$ and taking into account 4-time dilution of the blood sample on MX concentration via the expression:

$$C^0_{t\ BAS\ (MX)} = 4 \times C_{tBAS\ (MX)}^{sample} \quad (2)$$

the concentration $C_{t\ BAS(MX)}$ of BAS (MX) nonbound with form elements of blood is determined in blood of a patient.

5.10. For determination of the initial concentration of BAS (MX) the amendment on item 3.11 is entered:

$C^0_{t\ BAS\ (MX)}$—38.4%

$C_{t\ BAS\ (MX)}^{initial}$—100%

$$C_{t\ BAS\ (MX)}^{initial} = C_{tBAS\ (MX)}^{sample} \times 100/38.4 = 4 \times 2.6 \times C^0_{t\ BAS\ (MX)} \quad (3)$$

The minimum concentration of BAS (MX), that is determined in blood of a patient by means of the offered technique based on the measurement of the optical signal generated by the liquid-crystalline DNA dispersion with a dichrograph "Jobin-Yvon, Mark III" (France), makes $5 \times 10^{-7}$ M.

BEST MODE OF CARRYING OUT THE INVENTION

Below a specific example of fulfilment of the offered device for realization of the offered method with the references to the applied figures is given.

The device for the determination of BAS in an analyzed liquid designed according to the invention comprises: the source 1 (FIG. 10) of light radiation made, for example, on the base of the xenon lamp with air cooling; the selector 2 of light radiation wavelengths forming a light flow in a certain narrow spectral interval of wavelengths; the polarizer 3 designed, for example, as a prism of a nonlinear crystal material, fixed after the selector 2 and forming a linearly polarized light flow of the specified one; the modulator 4 of polarization, for example, of a photoelastic type, made of quartz, placed behind the polarizer 3 and transforming the linearly polarized light flow into a circular-polarized light flow with a periodically varied direction of rotation of its polarization vector; the cell 5 for placing of the analysed sample which contains a mixture prepared according to the method described above of the analyzed liquid containing BAS and the lyotropic cholesteric liquid-crystalline DNA dispersion; the photodetector 6 with the photosensitive surface that is oriented in the direction of the specified cell 5 and that transforms the optical signal generated by the specified liquid-crystalline dispersion into a proportional electrical signal. The photodetector 6 has two outputs 7, 8, one 7 of which is connected to an entry of control of the power supply 9 of the photodetector 6, and another one 8 is connected to the first entry 10 of the synchronous amplifier 11, output 12 of which is connected to an entry 13 of the unit 14 for processing the received electrical signal and for calculation of the concentration of the biologically active substance, other entry 15 of the specified processing unit is connected to the first output 16 of the control module 17, the second output 18 of the control module 17 is connected to the modulator 14 of polarization, the third output 19 of the control module 17 is connected to the selector 2, and the fourth its output 20 is connected to the second entry 21 of the synchronous amplifier 11.

As the unit 14 for processing the received electrical signal and calculation of the concentration of BAS, a personal computer, for example, or any other means destined for the similar purposes can be used.

The selector 2 forming the light flow of the certain wavelength can have various constructive designs, the common advantages of them are a minimum number of optical elements that is necessary for receiving the maximum output light flow at conservation of the required resolution and measurement accuracy (a high light flow transmittance), and the presence in the selector 2 of the electrodynamic driver 22 of the positional type ensuring a turn of one (or several) optical elements with a possibility of setting two chosen for the determined BAS wavelengths at which the CD signal measuring is produced (for example, a known electrodynamic driver is described in [Nesteruk I. N., Kompanets O. N., Mishin V. I., Russian Journal: Kwantovaya Elektronika, 1988, 15, N3, p.p.455–459].

In FIG. 11 the selector 2 is shown representing the simple wavelength tuned monochromator 23 comprising fixed on the general basis 24 the entry slit 25 and three optical elements 26, 27, 28. One of the optical elements represents the collimating mirror 26, the second optical element is the focusing mirror 27, and the third optical element is the dispersive element 28, designed as the plane diffraction grating. The concave surface 29 of the collimating mirror 26 is oriented in the direction of the entry slit 25 and the working surface 30 of the dispersive element 28. The concave surface 31 of the focusing mirror 27 is oriented simultaneously in the direction of the working surface 30 of the diffraction grating and the output slit 32 located in front of the mirror and made similarly to the entry slit 25.

The electrodynamic driver 22 of the positional type has the motor 33 (FIG. 12) comprising the stator (not shown in the FIG. 12) and the rotor 34 fixed on the shaft 35 of the motor 33. Besides the driver 22 has the transducer 36 of a turn angle of the rotor 34 located on one axis with the motor 33 and representing an inductive differential converter of a turn angle of the rotor 34 into an electrical signal. The transducer 36 has the modulator 37 fixed on the shaft 35 of the motor 33 with the eccentricity "e" concerning the rotation axis 38 of the rotor 34.

The rotor 34 of the motor 33 is designed as a ring consisting of a set of permanent magnets 39 and intermediate legs 40. Windings of the motor 33 are formed by several coils 41 with the wire 42 located motionlessly on the stator along the ring of the rotor 34. The ring of the rotor 34 is rigidly connected to the shaft 35 of the motor 33 located perpendicularly to the plane of FIG. 12.

The turn angle transducer 36 contains two coils 43 placed on legs 44 with pole tips 45 located diametrically opposite concerning the modulator 37, in addition the geometrical centre A of the modulator 37 is displaced relatively to the common axis of rotation of the motor 33 and the turn angle transducer 36 by the eccentricity "e". The specified eccentricity "e" allows to realize the amplitude dependence of the output signal of the turn angle transducer 36 upon the turn angle of the rotor 34 of the motor 33.

One optical element 26 or 27 or 28 of the monochromator 23 should be fixed on the shaft 35 of the motor 33 of the electrodynamic driver 22 with a possibility to turn around its own axis lying on the working surface of this element.

In FIG. 11 a mode is presented when the dispersive element 28, namely, the plane diffraction grating, is fixed on the shaft 35 of the motor 33. In addition any other element destined for similar purposes, for example, the optical prism can be used as the dispersive element 28. By the dotted line in FIG. 11 the version is shown when the focusing mirror 27 is fixed on the shaft 35 of the motor 33, thereat the dispersive element 28 and the second optical elements 26, namely, the collimating mirror, should be fixed motionlessly.

The designed mode of the simple monochromator is possible when the monochromator contains fixed on the general basis the entry and output slits, the collimating mirror and the dispersive element having a concave working surface. The concave surface of the mirror is oriented in the direction of the entry slit and the working surface of the dispersive element which in this case can represent a concave diffraction grating, its concave surface is oriented simultaneously in the direction of the output slit made similarly to the entry slit.

In the case when the light source 1 of light radiation forms a gathering light beam, it is possible even more simple mode of the simple monochromator design when the monochromator contains fixed on the general basis the entry and output slits and the dispersive element that represents a concave diffraction grating, and its concave working surface is oriented simultaneously in the direction of the entry and output slits.

In other design mode of the present invention the selector 46 (FIG. 13) comprises a great number of optical elements 47 being a set of narrow-band interference filters 47, each of them has a passband in the range of the certain wavelength. The filters 47 are fixed on the shaft 35 of the electrodynamic driver 22 by means of the cassette 48 with a possibility of their serial introduction into the light flow having the direction shown in FIG. 13 by the arrow B. The quantity of filters 47 depends on the amount of varieties of a biologically active substance that are required to be determined by means of the offered device.

The device works as follows.

According to the method described above, a set of control samples with different fixed concentrations of the certain substance to be analysed is prepared, and the measurement of signals of the circular dichroism is carried out consistently at two wavelengths for each sample, one measurement is done at the wavelength 270 nm, and another one at the wavelength that is characteristic for the present analyzed substance. Using the received meanings, the signals of circular dichroism for characteristic wavelengths are normalized on the signals corresponding to the wavelength 270 nm, for every pair of meanings. The calculated normalized values and the appropriate concentrations of the analyzed substance are written into a memory of the computer, and the diagram is built of the dependence of the normalized signal upon the concentration of the BAS, i.e. the calibration curve, that is marked in the computer.

Further, according to the method described above, the analyzed sample is prepared containing a mixture of the prepared before analyzed liquid containing the biologically active substance and of the lyotropic liquid-crystalline DNA dispersion formed in a polymer that is neutral in relation to the DNA. After this procedure the sample is put into the cell 5 of the offered device, and the device is switched on.

The source 1 of the light radiation radiates a broad-band light flow that enters the entry slit 25 of the selectors 2 of wavelengths, and the narrow-band light flow with one known wavelength is radiated from the selector 2 through its output slit 32. This light flow passes through the polarizer 3, becomes linearly polarized with the certain direction of the polarization vector, gets then into the optical entry of the modulator 4 of polarization, passing through which it becomes circular-polarized with a periodically varied direction of rotation of the polarization vector rotating in the plane that is perpendicular to the optical axis of the device. Then, passing the cell 5 with the analyzed sample possessing the abnormal optical activity or, in other words, the circular dichroism, the light flow becomes modulated on its intensity. Under action of light the electrical signal appears on the outputs 7, 8 of the photodetector 6, and on the output 8 the variable product is registered that is proportional to $\Delta A$ (the value of the signal caused by the abnormal optical activity), and on the output 7 the permanent product is registered that is proportional to A (the value of the signal describing absorption of the biologically active substance of the sample), thereat the frequency of the variable product is equal to the modulation frequency of light polarization. In the present device the permanent product is maintained at the fixed level by regulation of the power supply voltage of the photodetector 6, for that the signal of the permanent product from the output 7 of the photodetector 6 is put on the entry of control of its power supply 9, i.e. a mode of stabilization of the permanent product is realized by means of an inverse feedback on the permanent product with simultaneous measurement of the variable product, that is equivalent to measurement of their ratio, and so, to measurement of the signal of circular dichroism of the sample to be analysed. From the output 8 of the photodetector 6 the signal comes in the first entry 10 of the synchronous amplifier 11, to the second entry 21 of the photodetector 6 the reference signal is put at the frequency of modulation of polarization. In the synchronous amplifier 11 the signal is amplified, transformed into the direct current and directed to the processing unit 14 for processing, where it is transformed into the digital form, processed, compared with the calibration curve and put out as the meaning of the concentration in the sample of the biologically active substance being under test. The control module 17 realizes necessary interaction of all units of the device, realizes the required algorithm of processing, produces the voltage with a modulation frequency for work of the modulator 4 of polarization, forms the reference signal for functioning of the synchronous amplifier 11. The way of processing the received signal in the digital form depends on the type of the processing unit used for this purpose.

The electrodynamic driver 22 of the positional type of the selector 2 works as follows.

The transducer 36 of a turn angle of the rotor 34 produces an electrical signal, the amplitude of this signal depends on the turn angle of the shaft 35 of the motor 33 due to the presence of eccentricity "e" in a position of the modulator 37 of the transducer 36 concerning the axis 38 of rotation of the motor 33. At turn of the shaft 35 of the motor 33, a bore between the pole tips 45 and the modulator 37 varies and, hence, an amplitude of the signal of the transducer 36 of a turn angle of the rotor 34 varies as well. This signal enters the control module 17, where its meaning is compared with the meaning that corresponds to the certain wavelength of the selector 2, and their difference is determined. Depending on this difference the control module 17 produces the control signal directed to the coils 41 of the stator of the motor 33. The magnetic field caused by a current of the control signal flowing in the coils 41 of the stator of the motor 33 interacts with the magnetic field of the permanent magnets 39 of the rotor 34 of the motor 33 in such a manner that the rotor 34, and so, the shaft 35 of the motor 33 turns on the angle corresponding to the required wavelength of the selector 2, in dependence on the amplitude of the control signal.

In the case of usage of the monochromator 23 as the selector 2 the principle of its action does not differ from the principle of action of well known diffraction monochromators designed on the Czerny-Turner scheme [M. Czerny, A. F. Turner and M. V. R. K. Murty. Principles of Monochromators, Spectrometers and Spectrographs. Optical Engineering, vol. 13, N1, 1974, pp.23–38].

The difference is that the electrodynamic driver 22 of the positional type controlled by the signal coming from the control module 17 of the device is used as an arrangement for turn of one of optical elements 26, 27, 28 of the monochromator 23 for wavelength tuning.

In one mode of the monochromator design described above and shown in FIG. 11, the light from the light radiation source 1 through the slit 25 comes to the collimating mirror 26 that directs a parallel light beam to the diffraction grating 28 which forms a light flow of the required wavelength. It after reflection from the concave surface of the focusing mirror 27 is focused on the output slit 32 and comes through it to the polarizer 3. In another mode of the monochromator design described above, the light from the light radiation source 1 through the entry slit comes to the collimating mirror that directs a parallel light beam to the concave working surface of the diffraction grating. The light flow of of the required wavelength is focused on the output slit and comes through it to the polarizer 3.

In one more mode of the monochromator design, the light from the light radiation source 1 through the entry slit comes to the concave surface of the diffraction grating. The light flow of the required wavelength is focused on the output slit and comes through it to the polarizer 3.

In the case of usage of a set of the interference filters 47 as the selector 2 the device works as follows. The light flow from the light radiation source 1 passes through one of the mentioned above filters 47 located on a way of the light flow at the moment, and it is transformed on the output into the light flow with the required wavelength defined with the passband of the present filter 47. At necessary changes of the wavelength, the control signal from the control module 17 enters the motor 33 of the electrodynamic driver 22 of the positional type causing a turn of the shaft 35 of the motor 33 on other angle, so another filter 47 made for another wavelength is entered to the light flow, and the output light flow gets the wavelength defined by the passband of this filter 47.

Below examples of realization of the offered method with using the offered device are shown.

EXAMPLE 6

Analytical Possibilities of the Device

To check the correctness of the CD measurements and the reception of the authentic information about the optical properties of the analyzed liquids with the help of the offered device its calibration has been carried out with the use of the aqueous solution of n-propylammonium salt of d-10-camphorsulphonic acid and the aqueous-salt solution of the linear B-form double-stranded DNA.

6A. Calibration of the device with the use of the aqueous solution of n-propylammonium salt of d-10-camphorsulphonic acid and the aqueous-salt solution of the linear B-form double-stranded DNA.

6A.1. The aqueous solution of n-propylammonium salt of d-10-camphorsulphonic acid ($C_{10}H_{16}O_4S$) is usually applied for calibration of standard commercial dichrographs and spectropolarimeters. The CD spectrum of the aqueous solution of this acid (at certain concentration and temperature) is characterized by the presence of the positive band located in the UV-region of the spetrum (230–320 nm). The shape of this band, the exact position of its maximum, the amplitude of this band are in details described [Gillon M. F., Williams R. E. (1975). Can. J. Chem., 53, pp.2351–2353].

For calibration of the device, the aqueous solution of $C_{10}H_{16}O_4S$ with concentration 0.15 mg/ml was used. For this purpose 2 ml of aqueous solution of the specified concentration were placed into the rectangular optical quartz cell of the device (optical path length=1 cm), and its CD spectrum in the region of wavelengths 250–350 nm was registered by the device.

The CD spectrum of the solution, observable on the screen of the monitor of the computer connected with the device, is shown in FIG. 14.

In the CD spectrum of the solution in the region of wavelengths 250–320 nm the positive band is present, its amplitude and the maximum position ($\lambda$=290 nm) completely coincide with the literature data (see above).

6A.2. The well known in the literature conservative CD spectrum of the linear B-form double-stranded DNA is characterized by the presence of two bands of different signs with the approximately equal amplitudes. The positive band has a maximum at $\lambda$~278 nm, and the negative band—at $\lambda$~247 nm. One more "control" point in the CD spectrum of the linear B-form double-stranded DNA is the wavelength, at which molecular optical activity of the DNA aqueous-salt solution, changing its sign, becomes "zero". According to the literature data [Results of science and engineering (1975), vol. 1, ed. by Volkenstein M. V., VINITI, Moscow, p.115] this optical effect is observed at $\lambda$~258 nm.

For calibration of the device, the aqueous-salt solution of the linear B-form double-stranded DNA ($C_{DNA}$~5 $\mu$g/ml; 0.3 M NaCl+$10^{-2}$ M phosphate buffer) prepared according to items 1.1, 1.2 and 1.4 was used.

2 ml of the aqueous-salt DNA solution was placed into the rectangular optical quartz cell of the device (optical length 1 cm), and its CD spectrum in the region of wavelengths 240–310 nm was registered by means of the device.

In FIG. 15 the CD spectrum of the solution, observable on the screen of the monitor of the computer connected with the portable device, is presented.

Registered with the help of the device the CD spectrum (FIG. 15) completely repeats the above described peculiarities of the conservative CD spectrum of the linear B-form double-stranded DNA.

Thus, the results received in item 6A testify reliability of registration of the optical properties of the analyzed solutions by means of the offered device.

6B. Determination of optical properties of the liquid-crystalline DNA dispersion and the liquid-crystalline dispersions of (DNA-MX) complexes by the offered device.

6B.1. 2 ml of the liquid-cryslalline DNA dispersion ($C_{DNA}$~5 $\mu$g/ml; $C_{PEG}$=170 mg/ml; 0.3 M NaCl+$10^{-2}$ M phosphate buffer) prepared according to the example 1 are placed into the rectangular quartz cell of the device (optical length 1 cm), and its CD spectrum in the region of wavelengths 240–310 nm is registered by means of the device.

In FIG. 16 the observable CD spectrum of the liquid-crystalline DNA dispersion is shown. This spectrum is characterized by the presence of the intensive negative band, its shape, sign, amplitude and maximum position ($\lambda$~270 nm) completely correspond to the data presented in FIG. 2 (example 1) received by means of the standard laboratory "Jobin-Yvon" dichrograph.

6B.2. 4 $\mu$l of the solution prepared on item 2.1 are added to 2 ml of the liquid-crystalline DNA dispersion (item 6B.1) contained in the optical cell of the device; the mixture obtained in the cell is stirred during 30 s, and its CD spectrum in the region of wavelengths 580–720 nm is registered by the offered device.

In FIG. 17 the CD spectrum of such the liquid-crystalline dispersion treated with MX in the region of wavelengths from 580 up to 720 nm is shown. The addition of MX is accompanied by the appearance in the CD spectrum of the intensive negative band in the region of MX absorption, that is characterized by the presence of two maxima at $\lambda$~680 nm and $\lambda$~620 nm, that corresponds to the literature data. The appearance of this band testifies the formation of the liquid-crystalline dispersion from the (DNA-MX) complex (see p.18).

Thus, the results obtained convincingly testify that the device can be used for determination of MX in analyzed samples.

6C. Checking analytical possibilities of the device on the liquid-crystalline dispersions of the (DNA-MX) complexes.

6C.1. 2 ml of the liquid-crystalline DNA dispersion ($C_{DNA}$~5 $\mu$g/ml; $C_{PEG}$=170 mg/ml; 0.3 M NaCl+$10^{-2}$ M phosphate buffer) are placed into the rectangular quartz cell of the device (optical length 1 cm), and its abnormal optical activity at $\lambda$=270 nm is registered by the device.

6C.2. 1 $\mu$l-portions of the aqueous-salt MX solution ($C_{MX}$=0.2 mg/ml (3.868×$10^{-4}$ M); 0.3 M NaCl+$10^{-2}$ M phosphate buffer), altogether 4 portions (the total volume of the added solution is 4 $\mu$l) are added to 2 ml of the liquid-crystalline DNA dispersion (item 6C.1) contained in the optical cell. After each added portion of MX the mixture obtained in the optical cell is stirred (30 s), and its abnormal optical properties at $\lambda$=270 nm are registered by the device.

6C.3. The data received in the measurements at $\lambda$=270 nm (item 6C.2) are compared with the results of the measurement carried out in item 6C.1. If the results of these measurements differ not more than 5%, one can begin to registrate the optical signal at $\lambda$=680 nm generated by the liquid-crystalline DNA dispersion as a result of a complex formation with MX molecules added (item 6C.2) to the solution.

6C.4. In complete agreement with items 6C.1–6C.3 one more titration of the liquid-crystalline DNA dispersion (item 6C.1) is produced with the aqueous-salt MX solution with smaller MX concentration ($C_{MX}$=0.02 mg/ml (3.868×$10^{-5}$ M; 0.3 M NaCl+$10^{-2}$ M phosphate buffer).

The results obtained during checking analytical possibilities of the device with the use of the liquid-crystalline dispersions of (DNA-MX) complexes have shown (FIG. 18) that, as well as in the case of the data obtained with help of "Jobin-Yvon" dichrograph (FIG. 5, example 2), the directly proportional dependence is observed between the value of the optical signal generated by the liquid-crystalline DNA dispersion at $\lambda$=680 nm at the formation of the (DNA-MX) complex and the Ct MX value. This dependence shows that due to the device one can determine the presence and the concentration of MX in analyzed samples.

The check has shown that a large advantage of the device is that it allows quickly and precisely to determine MX in a wide range of concentrations including concentrations from $5 \times 10^{-7}$ down to $5 \times 10^{-8}$ M, i.e. one order of magnitude lower than limit concentrations detected by the known devices of "Jobin-Yvon" and "Jasco" firms.

Thus, the offered method and the offered device allow quickly, precisely and with a high sensitivity to determine the presence and the concentrations of BAS (MX) in blood of patients, whose therapy is connected with application of antitumor compounds.

The offered method excludes the use of complex and expensive equipment and the presence of a highly skilled personnel as well, and can be used for determination of other biologically active and pharmacological compounds forming intercalation complexes with DNA bases pairs.

INDUSTRIAL APPLICABILITY

The offered invention can be used in medical and clinical biochemistry, and also for molecular pharmacology at research of pharmaco-kinetics of biologically active substances, for pharmaceutical industry and ecology. The most effective its use is in clinical biochemistry.

What is claimed is:

1. The method for determination in an analyzed liquid of a biologically active substance interacting with a lyotropic cholesteric liquid-crystalline DNA dispersion formed in a polymer neutral in respect to DNA, distinguished by:

that the lyotropic cholesteric liquid-crystalline dispersion is formed in an aqueous-salt solution of the specified polymer of the linear double-stranded DNA molecules of a low molecular mass immediately before mixing with the analyzed liquid containing the determined biologically active substance, thereat the analysed liquid is previously mixed with the specified polymer under conditions, when the optical properties of the lyotropic liquid-crystalline DNA dispersion are not broken, then through the analysed sample, obtained as a result of mixing of the prepared analyzed liquid with the specified liquid-crystalline DNA dispersion, a flow of circular-polarized light is passed, and the optical signal is registered generated by the liquid-crystalline dispersion at two wavelengths, one of them is in the region of the DNA absorption, and another one is in the region of absorption of the determined biologically active substance, then the ratio is calculated between these signals at the specified wavelengths, and the concentration of the biologically active substance is determined on this ratio using the calibration curve.

2. The method on item 1, distinguished by that polyethyleneglycol is used as the neutral polymer.

3. The method on item 1, distinguished by that a biological liquid is used as the analyzed liquid.

4. The method on item 3, distinguished by that blood is used as the biological liquid.

5. The method on item 3, distinguished by that plasma of blood is used as the biological liquid.

6. The method on item 1, distinguished by that the biologically active substance represents an antitumor substance of the anthraquinone group.

7. The method on item 6, distinguished by that the antitumor substance of the anthraquinone group represents a mithoxantrone.

8. The method on item 3, distinguished by that at determination of the biologically active substance in the biological liquid with heterogeneous in it distribution of the biologically active substance, its concentration obtained due to the calibration curve is corrected in view of factor of its distribution in the biological liquid.

9. The device for determination of a biologically active substance in an analyzed liquid, comprising installed consistently:

Source (1) of light radiation;

Selector (2) having at least one optical element (26, 27, 28, 47) and forming a light flow of a certain wavelength;

Polarizer (3) forming a linearly polarized light flow of the specified light flow;

Modulator (4) of polarization transforming the linearly polarized light flow into a circular-polarized light flow with a periodically varied direction of rotation of its polarization vector;

Cell (5) for an analysed sample;

Photodetector (6) transforming the optical signal generated by components of the sample to be analyzed into the proportional electrical signal;

Synchronous amplifier (11) increasing the pointed electrical signal;

Processing unit (14) for processing the received electrical signal and for calculation of concentration of the biologically active substance;

Control module (17), distinguished by that the selector (2) contains an electrodynamic driver (22) of a positional type, designed with a possibility of setting at least two wavelengths, at which the optical signal generated by the components of the sample under analysis is registered, and at least one optical element (26, 27, 28, 47) fixed on a motor (33) shaft (35) of the specified driver (22).

10. The device on item 9, distinguished by that the selector (2) represents a simple monochromator (23) containing at least two optical elements (26, 28), one of them represents a dispersive element (28), and one of these optical elements (26 or 28) is fixed on the motor (33) shaft (35) of the specified driver (22) with the possibility to turn around its own axis.

11. The device on item 10, distinguished by that the dispersive element (28) represents a diffraction grating.

12. The device on item 11, distinguished by that the diffraction grating (28) is designed concave.

13. The device on item 9, distinguished by that the selector (2) represents a simple monochromator (23) containing one optical element (28) fixed on the motor (33) shaft (35) of the specified driver (22) with the possibility to turn around its own axis and representing the dispersive element (28) designed as the concave diffraction grating.

14. The device on item 9, distinguished by that the selector (2) contains a grate number of optical elements (47) being a set of narrow-band interference filters (47) fixed on the motor (33) shaft (35) of the specified driver (22) with a possibility of their alternate introduction into the light flow, in addition each of these filters (47) has a transparency band in the region of the certain wavelength chosen for the concrete biologically active substance.

15. The device on item 9, distinguished by that the electrodynamic driver (22) contains the transducer (36) of a turn angle of its motor (33) rotor (34), representing an inductive differential converter of a turn angle of the rotor (34) into an appropriate electrical signal, and containing a modulator (37) designed as a ring fixed on the motor (33) shaft (35) with an eccentricity ("e") concerning its rotation axis (38).

* * * * *